(12) United States Patent
Ivri et al.

(10) Patent No.: US 7,290,541 B2
(45) Date of Patent: Nov. 6, 2007

(54) AEROSOL DELIVERY APPARATUS AND METHOD FOR PRESSURE-ASSISTED BREATHING SYSTEMS

(75) Inventors: Ehud Ivri, Newport Beach, CA (US); James Fink, San Mateo, CA (US)

(73) Assignee: Aerogen, Inc., Mountain View, CA (US)

( * ) Notice: Subject to any disclaimer, the term of this patent is extended or adjusted under 35 U.S.C. 154(b) by 211 days.

(21) Appl. No.: 10/883,115

(22) Filed: Jun. 30, 2004

(65) Prior Publication Data

US 2005/0229928 A1    Oct. 20, 2005

Related U.S. Application Data

(63) Continuation-in-part of application No. 10/828,765, filed on Apr. 20, 2004.

(51) Int. Cl.
*A61M 11/00* (2006.01)
*A61M 15/00* (2006.01)

(52) U.S. Cl. .............. 128/200.14; 128/203.12

(58) Field of Classification Search ......... 128/200.16, 128/203.12, 204.18, 204.23, 200.14
See application file for complete search history.

(56) References Cited

U.S. PATENT DOCUMENTS

| | | | |
|---|---|---|---|
| 550,315 A | 11/1895 | Allen | |
| 809,159 A | 1/1906 | Willis et al. | |
| 1,680,616 A | 8/1928 | Horst | |
| 2,022,520 A | 11/1935 | Philbrick | |
| 2,101,304 A | 12/1937 | Wright | |
| 2,158,615 A | 5/1939 | Wright | |
| 2,187,528 A | 1/1940 | Wing | |
| 2,223,541 A | 12/1940 | Baker | |
| 2,266,706 A | 12/1941 | Fox et al. | |
| 2,283,333 A | 5/1942 | Martin | |
| 2,292,381 A | 8/1942 | Klagges | |
| 2,360,297 A | 10/1944 | Wing | |
| 2,375,770 A | 5/1945 | Dahlberg | |
| 2,383,098 A | 8/1945 | Wheaton | |
| 2,404,063 A | 7/1946 | Healy | |
| 2,430,023 A | 11/1947 | Longmaid | |

(Continued)

FOREIGN PATENT DOCUMENTS

CH    477 885    9/1969

(Continued)

OTHER PUBLICATIONS

Berggren, E. "Pilot Study of Nebulized Surfactant Therapy for Neonatal Respiratory Distress Syndrome", Acta Paediatr 89: 460-464, Taylor & Francis, ISSN 0803-5253, 2000, Sweden.

(Continued)

*Primary Examiner*—Quang D. Thanh
(74) *Attorney, Agent, or Firm*—Townsend and Townsend and Crew

(57) ABSTRACT

A pressure-assisted breathing system comprises a flow generator, a circuit connecting the flow generator to a patient's respiratory system and an aerosol generator for emitting aerosol particles into the circuit, wherein the circuit defines a path for the emitted aerosol particles having a change in angle no greater than 15°.

26 Claims, 9 Drawing Sheets

U.S. PATENT DOCUMENTS

| | | |
|---|---|---|
| 2,474,996 A | 7/1949 | Wallis |
| 2,512,004 A | 6/1950 | Wing |
| 2,521,657 A | 9/1950 | Severy |
| 2,681,041 A | 6/1954 | Zodtner et al. |
| 2,705,007 A | 3/1955 | Gerber |
| 2,735,427 A | 2/1956 | Sullivan |
| 2,764,946 A | 10/1956 | Henderson |
| 2,764,979 A | 10/1956 | Henderson |
| 2,779,623 A | 1/1957 | Eisenkraft |
| 2,935,970 A | 5/1960 | Morse et al. |
| 3,103,310 A | 9/1963 | Lang |
| 3,325,031 A | 6/1967 | Singier |
| 3,411,854 A | 11/1968 | Rosler et al. |
| 3,515,348 A | 6/1970 | Coffman, Jr. |
| 3,550,864 A | 12/1970 | East |
| 3,558,052 A | 1/1971 | Dunn |
| 3,561,444 A | 2/1971 | Boucher |
| 3,563,415 A | 2/1971 | Ogle |
| 3,680,954 A | 8/1972 | Frank |
| 3,719,328 A | 3/1973 | Hindman |
| 3,738,574 A | 6/1973 | Guntersdorfer et al. |
| 3,771,982 A | 11/1973 | Dobo |
| 3,790,079 A | 2/1974 | Berglund et al. |
| 3,804,329 A | 4/1974 | Martner |
| 3,812,854 A * | 5/1974 | Michaels et al. ...... 128/200.16 |
| 3,838,686 A | 10/1974 | Szekely |
| 3,842,833 A | 10/1974 | Ogle |
| 3,865,106 A | 2/1975 | Palush |
| 3,903,884 A | 9/1975 | Huston et al. |
| 3,906,950 A | 9/1975 | Cocozza |
| 3,908,654 A | 9/1975 | Lhoest et al. |
| 3,950,760 A | 4/1976 | Rauch et al. |
| 3,951,313 A | 4/1976 | Coniglione |
| 3,958,249 A | 5/1976 | DeMaine et al. |
| 3,970,250 A | 7/1976 | Drews |
| 3,983,740 A | 10/1976 | Danel |
| 3,993,223 A | 11/1976 | Welker, III et al. |
| 4,005,435 A | 1/1977 | Lundquist et al. |
| 4,020,834 A | 5/1977 | Bird |
| 4,030,492 A | 6/1977 | Simburner |
| 4,052,986 A | 10/1977 | Scaife |
| 4,059,384 A | 11/1977 | Holland et al. |
| D246,574 S | 12/1977 | Meierhoefer |
| 4,076,021 A | 2/1978 | Thompson |
| 4,083,368 A | 4/1978 | Freezer |
| 4,094,317 A | 6/1978 | Wasnich |
| 4,101,041 A | 7/1978 | Mauro, Jr. et al. |
| 4,106,503 A | 8/1978 | Rsenthal et al. |
| 4,109,174 A | 8/1978 | Hodgson |
| 4,113,809 A | 9/1978 | Abair et al. |
| D249,958 S | 10/1978 | Meierhoefer |
| 4,119,096 A | 10/1978 | Drews |
| 4,121,583 A | 10/1978 | Chen |
| 4,159,803 A | 7/1979 | Cameto et al. |
| 4,207,990 A | 6/1980 | Weiler et al. |
| 4,210,155 A | 7/1980 | Grimes |
| 4,226,236 A | 10/1980 | Genese |
| 4,240,081 A | 12/1980 | Devitt |
| 4,240,417 A | 12/1980 | Holever |
| 4,248,227 A | 2/1981 | Thomas |
| 4,261,512 A | 4/1981 | Zierenberg |
| D259,213 S | 5/1981 | Pagels |
| 4,268,460 A | 5/1981 | Boiarski et al. |
| 4,294,407 A | 10/1981 | Reichl et al. |
| 4,298,045 A | 11/1981 | Weiler et al. |
| 4,299,784 A | 11/1981 | Hense |
| 4,300,546 A | 11/1981 | Kruber |
| 4,301,093 A | 11/1981 | Eck |
| 4,319,155 A | 3/1982 | Makai et al. |
| 4,334,531 A | 6/1982 | Reichl et al. |
| 4,336,544 A | 6/1982 | Donald et al. |
| 4,338,576 A | 7/1982 | Takahashi et al. |
| 4,340,044 A * | 7/1982 | Levy et al. ............ 128/204.21 |
| 4,368,476 A | 1/1983 | Uehara et al. |
| 4,368,850 A | 1/1983 | Szekely |
| 4,374,707 A | 2/1983 | Pollack |
| 4,389,071 A | 6/1983 | Johnson, Jr. et al. |
| 4,408,719 A | 10/1983 | Last |
| 4,428,802 A | 1/1984 | Kanai et al. |
| 4,431,136 A | 2/1984 | Janner et al. |
| 4,454,877 A | 6/1984 | Miller et al. |
| 4,465,234 A | 8/1984 | Maehara et al. |
| 4,474,251 A | 10/1984 | Johnson, Jr. |
| 4,474,326 A | 10/1984 | Takahashi |
| 4,475,113 A | 10/1984 | Lee et al. |
| 4,479,609 A | 10/1984 | Maeda et al. |
| 4,484,577 A * | 11/1984 | Sackner et al. ........ 128/203.28 |
| 4,502,481 A * | 3/1985 | Christian ............... 128/205.24 |
| 4,512,341 A | 4/1985 | Lester |
| 4,530,464 A | 7/1985 | Yamamoto et al. |
| 4,533,082 A | 8/1985 | Maehara et al. |
| 4,539,575 A | 9/1985 | Nilsson |
| 4,544,933 A | 10/1985 | Heinzl |
| 4,546,361 A | 10/1985 | Brescia et al. |
| 4,550,325 A | 10/1985 | Viola |
| 4,566,452 A | 1/1986 | Farr |
| 4,591,883 A | 5/1986 | Isayama |
| 4,593,291 A | 6/1986 | Howkins |
| 4,605,167 A | 8/1986 | Maehara |
| 4,613,326 A | 9/1986 | Szwarc |
| 4,620,201 A | 10/1986 | Heinzl et al. |
| 4,628,890 A | 12/1986 | Freeman |
| 4,632,311 A | 12/1986 | Nakane et al. |
| 4,658,269 A | 4/1987 | Rezanka |
| 4,659,014 A | 4/1987 | Soth et al. |
| 4,677,975 A | 7/1987 | Edgar et al. |
| 4,678,680 A | 7/1987 | Abowitz |
| 4,679,551 A | 7/1987 | Anthony |
| 4,681,264 A | 7/1987 | Johnson, Jr. |
| 4,693,853 A | 9/1987 | Falb et al. |
| 4,702,418 A | 10/1987 | Carter et al. |
| 4,722,906 A | 2/1988 | Guire |
| 4,753,579 A | 6/1988 | Murphy |
| 4,790,479 A | 12/1988 | Matsumoto et al. |
| 4,793,339 A | 12/1988 | Matsumoto et al. |
| 4,796,807 A | 1/1989 | Bendig et al. |
| 4,799,622 A | 1/1989 | Ishikawa et al. |
| 4,805,609 A | 2/1989 | Roberts et al. |
| 4,819,629 A | 4/1989 | Jonson |
| 4,819,834 A | 4/1989 | Thiel |
| 4,826,080 A | 5/1989 | Ganser |
| 4,826,759 A | 5/1989 | Guire et al. |
| 4,828,886 A | 5/1989 | Hieber |
| 4,843,445 A | 6/1989 | Stemme |
| 4,849,303 A | 7/1989 | Graham et al. |
| 4,850,534 A | 7/1989 | Takahashi et al. |
| 4,852,563 A * | 8/1989 | Gross .................... 128/202.27 |
| 4,865,006 A | 9/1989 | Nogi et al. |
| 4,871,489 A | 10/1989 | Ketcham |
| 4,872,553 A | 10/1989 | Suzuki et al. |
| 4,877,989 A | 10/1989 | Drews et al. |
| 4,888,516 A | 12/1989 | Daeges et al. |
| 4,922,901 A | 5/1990 | Brooks et al. |
| 4,926,915 A | 5/1990 | Deussen et al. |
| 4,934,358 A | 6/1990 | Nilsson et al. |
| 4,951,661 A * | 8/1990 | Sladek .................. 128/202.27 |
| 4,954,225 A | 9/1990 | Bakewell |
| 4,957,239 A | 9/1990 | Tempelman |
| 4,964,521 A | 10/1990 | Wieland et al. |
| D312,209 S | 11/1990 | Morrow et al. |
| 4,968,299 A | 11/1990 | Ahlstrand et al. |
| 4,971,665 A | 11/1990 | Sexton |
| 4,973,493 A | 11/1990 | Guire |
| 4,976,259 A | 12/1990 | Higson et al. |

| | | |
|---|---|---|
| 4,979,959 A | 12/1990 | Guire |
| 4,994,043 A | 2/1991 | Ysebaert |
| 5,002,048 A | 3/1991 | Makiej, Jr. |
| 5,002,582 A | 3/1991 | Guire et al. |
| 5,007,419 A | 4/1991 | Weinstein et al. |
| 5,016,024 A | 5/1991 | Lam et al. |
| 5,021,701 A | 6/1991 | Takahashi et al. |
| 5,022,587 A | 6/1991 | Hochstein |
| 5,024,733 A | 6/1991 | Abys et al. |
| 5,046,627 A | 9/1991 | Hansen |
| 5,062,419 A | 11/1991 | Rider |
| 5,063,396 A | 11/1991 | Shiokawa et al. |
| 5,063,922 A * | 11/1991 | Hakkinen .............. 128/200.16 |
| 5,073,484 A | 12/1991 | Swanson et al. |
| 5,076,266 A | 12/1991 | Babaev |
| 5,080,093 A | 1/1992 | Raabe et al. |
| 5,080,649 A | 1/1992 | Vetter |
| 5,086,765 A | 2/1992 | Levine |
| 5,086,785 A | 2/1992 | Gentile et al. |
| 5,115,803 A | 5/1992 | Sioutas |
| 5,115,971 A | 5/1992 | Greenspan et al. |
| D327,008 S | 6/1992 | Friedman |
| 5,122,116 A | 6/1992 | Kriesel et al. |
| 5,129,579 A | 7/1992 | Conte |
| 5,134,993 A | 8/1992 | Van Der Linden et al. |
| 5,139,016 A | 8/1992 | Waser |
| 5,140,740 A | 8/1992 | Weigelt |
| 5,147,073 A | 9/1992 | Cater |
| 5,152,456 A | 10/1992 | Ross et al. |
| 5,157,372 A | 10/1992 | Langford |
| 5,164,740 A | 11/1992 | Ivri |
| 5,169,029 A | 12/1992 | Behar et al. |
| 5,170,782 A | 12/1992 | Kocinski |
| 5,180,482 A | 1/1993 | Abys et al. |
| 5,186,164 A | 2/1993 | Raghuprasad |
| 5,186,166 A | 2/1993 | Riggs et al. |
| 5,198,157 A | 3/1993 | Bechet |
| 5,201,322 A | 4/1993 | Henry et al. |
| 5,213,860 A | 5/1993 | Laing |
| 5,217,148 A | 6/1993 | Cater |
| 5,217,492 A | 6/1993 | Guire et al. |
| 5,227,168 A | 7/1993 | Chvapil |
| 5,230,496 A | 7/1993 | Shillington et al. |
| 5,245,995 A | 9/1993 | Sullivan et al. |
| 5,248,087 A | 9/1993 | Dressler |
| 5,258,041 A | 11/1993 | Guire et al. |
| 5,261,601 A | 11/1993 | Ross et al. |
| 5,263,992 A | 11/1993 | Guire |
| 5,279,568 A | 1/1994 | Cater |
| 5,297,734 A | 3/1994 | Toda |
| 5,299,739 A | 4/1994 | Takahashi et al. |
| 5,303,854 A | 4/1994 | Cater |
| 5,309,135 A | 5/1994 | Langford |
| 5,312,281 A | 5/1994 | Takahashi et al. |
| 5,313,955 A | 5/1994 | Rodder |
| 5,319,971 A | 6/1994 | Osswald et al. |
| 5,320,603 A | 6/1994 | Vetter et al. |
| 5,322,057 A | 6/1994 | Raabe et al. |
| 5,342,011 A | 8/1994 | Short |
| 5,342,504 A | 8/1994 | Hirano et al. |
| 5,347,998 A | 9/1994 | Hodson et al. |
| 5,348,189 A | 9/1994 | Cater |
| 5,350,116 A | 9/1994 | Cater |
| 5,355,872 A | 10/1994 | Riggs et al. |
| 5,357,946 A | 10/1994 | Kee et al. |
| 5,372,126 A | 12/1994 | Blau |
| 5,383,906 A | 1/1995 | Burchett et al. |
| 5,388,571 A | 2/1995 | Roberts et al. |
| 5,392,768 A | 2/1995 | Johansson et al. |
| 5,396,883 A | 3/1995 | Knupp et al. |
| 5,414,075 A | 5/1995 | Swan et al. |
| 5,415,161 A | 5/1995 | Ryder |
| 5,419,315 A | 5/1995 | Rubsamen |
| 5,426,458 A | 6/1995 | Wenzel et al. |
| 5,431,155 A | 7/1995 | Marelli |
| 5,435,282 A | 7/1995 | Haber et al. |
| 5,435,297 A | 7/1995 | Klein |
| 5,437,267 A | 8/1995 | Weinstein et al. |
| 5,445,141 A | 8/1995 | Kee et al. |
| D362,390 S | 9/1995 | Weiler |
| 5,449,502 A | 9/1995 | Igusa et al. |
| 5,452,711 A | 9/1995 | Gault |
| 5,458,135 A | 10/1995 | Patton et al. |
| 5,458,289 A | 10/1995 | Cater |
| 5,474,059 A | 12/1995 | Cooper |
| 5,477,992 A | 12/1995 | Jinks et al. |
| 5,479,920 A | 1/1996 | Piper et al. |
| 5,485,850 A | 1/1996 | Dietz |
| 5,487,378 A | 1/1996 | Robertson et al. |
| 5,489,266 A | 2/1996 | Grimard |
| 5,497,944 A | 3/1996 | Weston et al. |
| D369,212 S | 4/1996 | Snell |
| 5,511,726 A | 4/1996 | Greenspan et al. |
| 5,512,329 A | 4/1996 | Guire et al. |
| 5,512,474 A | 4/1996 | Clapper et al. |
| 5,515,841 A | 5/1996 | Robertson et al. |
| 5,515,842 A | 5/1996 | Ramseyer et al. |
| 5,516,043 A | 5/1996 | Manna et al. |
| 5,518,179 A | 5/1996 | Humberstone et al. |
| 5,529,055 A | 6/1996 | Gueret |
| 5,533,497 A | 7/1996 | Ryder |
| 5,537,997 A * | 7/1996 | Mechlenburg et al. . 128/204.23 |
| 5,542,410 A | 8/1996 | Goodman et al. |
| 5,549,102 A | 8/1996 | Lintl et al. |
| 5,560,837 A | 10/1996 | Trueba |
| 5,563,056 A | 10/1996 | Swan et al. |
| D375,352 S | 11/1996 | Bologna |
| 5,579,757 A | 12/1996 | McMahon et al. |
| 5,582,330 A | 12/1996 | Iba |
| 5,584,285 A * | 12/1996 | Salter et al. ........... 128/200.21 |
| 5,586,550 A | 12/1996 | Ivri et al. |
| 5,588,166 A | 12/1996 | Burnett |
| 5,601,077 A | 2/1997 | Imbert |
| 5,609,798 A | 3/1997 | Liu et al. |
| 5,632,878 A | 5/1997 | Kitano |
| 5,635,096 A | 6/1997 | Singer et al. |
| 5,637,460 A | 6/1997 | Swan et al. |
| 5,647,349 A | 7/1997 | Ohki et al. |
| 5,653,227 A | 8/1997 | Barnes et al. |
| 5,654,007 A | 8/1997 | Johnson et al. |
| 5,654,162 A | 8/1997 | Guire et al. |
| 5,654,460 A | 8/1997 | Rong |
| 5,657,926 A | 8/1997 | Toda |
| 5,660,166 A | 8/1997 | Lloyd |
| 5,664,557 A | 9/1997 | Makiej, Jr. |
| 5,664,706 A | 9/1997 | Cater |
| 5,665,068 A | 9/1997 | Takamura |
| 5,666,946 A | 9/1997 | Langenback |
| 5,670,999 A | 9/1997 | Takeuchi et al. |
| 5,685,491 A | 11/1997 | Marks et al. |
| 5,692,644 A | 12/1997 | Gueret |
| 5,694,923 A * | 12/1997 | Hete et al. .............. 128/204.18 |
| 5,707,818 A | 1/1998 | Chudzik et al. |
| 5,709,202 A | 1/1998 | Lloyd et al. |
| 5,714,360 A | 2/1998 | Swan et al. |
| 5,714,551 A | 2/1998 | Bezwada et al. |
| 5,718,222 A | 2/1998 | Lloyd et al. |
| D392,184 S | 3/1998 | Weiler |
| 5,724,957 A | 3/1998 | Rubsamen et al. |
| 5,744,515 A | 4/1998 | Clapper |
| 5,752,502 A | 5/1998 | King |
| 5,755,218 A | 5/1998 | Johansson et al. |
| 5,758,637 A | 6/1998 | Ivri et al. |
| 5,775,506 A | 7/1998 | Grabenkort |
| 5,788,665 A | 8/1998 | Sekins |
| 5,788,819 A | 8/1998 | Onishi et al. |

| | | | | | | |
|---|---|---|---|---|---|---|
| 5,790,151 A | 8/1998 | Mills | | 6,341,732 B1 | 1/2002 | Martin et al. |
| 5,810,004 A | 9/1998 | Ohki et al. | | 6,358,058 B1 | 3/2002 | Strupat et al. |
| 5,819,730 A | 10/1998 | Stone et al. | | 6,394,363 B1 | 5/2002 | Arnott et al. |
| 5,823,179 A | 10/1998 | Grychowski et al. | | 6,402,046 B1 | 6/2002 | Loser |
| 5,823,428 A | 10/1998 | Humberstone et al. | | 6,405,934 B1 | 6/2002 | Hess et al. |
| 5,829,723 A | 11/1998 | Brunner et al. | | 6,427,682 B1 | 8/2002 | Klimowicz et al. |
| 5,836,515 A | 11/1998 | Fonzes | | 6,443,146 B1 | 9/2002 | Voges |
| 5,839,617 A | 11/1998 | Cater et al. | | 6,443,366 B1 | 9/2002 | Hirota et al. |
| 5,842,468 A | 12/1998 | Denyer et al. | | 6,467,476 B1 | 10/2002 | Ivri et al. |
| 5,862,802 A | 1/1999 | Bird | | 6,467,477 B1 * | 10/2002 | Frank et al. ............ 128/203.23 |
| 5,865,171 A | 2/1999 | Cinquin | | 6,530,370 B1 | 3/2003 | Heinonen |
| 5,878,900 A | 3/1999 | Hansen | | 6,540,153 B1 | 4/2003 | Ivri |
| 5,893,515 A | 4/1999 | Hahn et al. | | 6,540,154 B1 | 4/2003 | Ivri et al. |
| 5,894,841 A | 4/1999 | Voges | | 6,543,443 B1 | 4/2003 | Klimowicz et al. |
| 5,897,008 A | 4/1999 | Hansen | | 6,546,927 B2 | 4/2003 | Litherland et al. |
| 5,910,698 A | 6/1999 | Yagi | | 6,550,472 B2 | 4/2003 | Litherland et al. |
| 5,915,377 A | 6/1999 | Coffee | | 6,554,201 B2 | 4/2003 | Klimowicz et al. |
| 5,918,637 A | 7/1999 | Fleischman | | 6,581,595 B1 | 6/2003 | Murdock et al. |
| 5,925,019 A | 7/1999 | Ljungquist | | 6,615,824 B2 | 9/2003 | Power |
| 5,938,117 A | 8/1999 | Ivri | | 6,629,646 B1 | 10/2003 | Ivri |
| 5,950,619 A | 9/1999 | Van Der Linden et al. | | 6,640,804 B2 | 11/2003 | Ivri |
| 5,954,268 A | 9/1999 | Joshi et al. | | 6,651,650 B1 | 11/2003 | Yamamoto et al. |
| 5,960,792 A | 10/1999 | Lloyd et al. | | 6,688,304 B2 | 2/2004 | Gonda et al. |
| 5,964,417 A | 10/1999 | Amann et al. | | 6,705,315 B2 | 3/2004 | Sullivan et al. |
| 5,970,974 A | 10/1999 | Van Der Linden et al. | | 6,705,316 B2 * | 3/2004 | Blythe et al. .......... 128/204.18 |
| 5,976,344 A | 11/1999 | Abys et al. | | 6,725,858 B2 * | 4/2004 | Loescher ............... 128/200.14 |
| 5,993,805 A | 11/1999 | Sutton et al. | | 6,732,944 B2 | 5/2004 | Litherland et al. |
| 6,000,396 A | 12/1999 | Melker et al. | | 6,745,768 B2 | 6/2004 | Colla et al. |
| 6,007,518 A | 12/1999 | Kriesel et al. | | 6,745,770 B2 | 6/2004 | McAuliffe et al. |
| 6,012,450 A | 1/2000 | Rubsamen | | 6,755,189 B2 | 6/2004 | Ivri et al. |
| 6,014,970 A | 1/2000 | Ivri et al. | | 6,769,626 B1 | 8/2004 | Haveri |
| 6,026,809 A | 2/2000 | Abrams et al. | | 6,782,886 B2 | 8/2004 | Narayan et al. |
| 6,029,666 A | 2/2000 | Aloy et al. | | 6,810,876 B2 | 11/2004 | Berthon-Jones |
| 6,032,665 A | 3/2000 | Psaros | | 6,814,071 B2 | 11/2004 | Klimowicz et al. |
| 6,037,587 A | 3/2000 | Dowell et al. | | 6,817,361 B2 | 11/2004 | Berthon-Jones et al. |
| 6,039,696 A | 3/2000 | Bell | | 6,840,240 B1 | 1/2005 | Berthon-Jones et al. |
| 6,045,215 A | 4/2000 | Coulman | | 6,845,770 B2 | 1/2005 | Klimowicz et al. |
| 6,045,874 A | 4/2000 | Himes | | 6,851,626 B2 | 2/2005 | Patel et al. |
| 6,047,818 A | 4/2000 | Warby et al. | | 6,860,268 B2 * | 3/2005 | Bohn et al. ............ 128/206.21 |
| 6,055,869 A | 5/2000 | Stemme et al. | | 6,904,906 B2 * | 6/2005 | Salter et al. ............ 128/200.21 |
| 6,060,128 A | 5/2000 | Kim et al. | | 2001/0013554 A1 | 8/2001 | Borland et al. |
| 6,062,212 A | 5/2000 | Davison et al. | | 2001/0015737 A1 | 8/2001 | Truninger et al. |
| 6,068,148 A | 5/2000 | Weiler | | 2002/0011247 A1 | 1/2002 | Ivri et al. |
| 6,085,740 A | 7/2000 | Ivri et al. | | 2002/0023650 A1 | 2/2002 | Gunaratnam et al. |
| 6,096,011 A | 8/2000 | Trombley, III et al. | | 2002/0033178 A1 | 3/2002 | Farrell et al. |
| 6,105,877 A | 8/2000 | Coffee | | 2002/0036601 A1 | 3/2002 | Puckeridge et al. |
| 6,106,504 A | 8/2000 | Urrutia | | 2002/0078958 A1 | 6/2002 | Stenzler |
| 6,116,234 A | 9/2000 | Genova et al. | | 2002/0104530 A1 | 8/2002 | Ivri et al. |
| 6,123,413 A | 9/2000 | Agarwal et al. | | 2002/0121274 A1 | 9/2002 | Borland et al. |
| 6,139,674 A | 10/2000 | Markham et al. | | 2002/0134372 A1 | 9/2002 | Loeffler et al. |
| 6,142,146 A | 11/2000 | Abrams et al. | | 2002/0134374 A1 | 9/2002 | Loeffler et al. |
| 6,145,963 A | 11/2000 | Pidwerbecki et al. | | 2002/0134375 A1 | 9/2002 | Loeffler et al. |
| 6,146,915 A | 11/2000 | Pidwerbecki et al. | | 2002/0134377 A1 | 9/2002 | Loeffler et al. |
| 6,152,130 A | 11/2000 | Abrams et al. | | 2002/0162551 A1 | 11/2002 | Litherland |
| 6,155,676 A | 12/2000 | Etheridge et al. | | 2002/0195107 A1 | 12/2002 | Smaldone |
| 6,158,431 A | 12/2000 | Poole | | 2003/0140921 A1 | 7/2003 | Smith et al. |
| 6,161,536 A | 12/2000 | Redmon et al. | | 2003/0145859 A1 | 8/2003 | Bohn et al. |
| 6,163,588 A | 12/2000 | Matsumoto et al. | | 2003/0150445 A1 | 8/2003 | Power et al. |
| 6,182,662 B1 | 2/2001 | McGhee | | 2003/0150446 A1 | 8/2003 | Patel et al. |
| 6,186,141 B1 | 2/2001 | Pike et al. | | 2003/0226906 A1 | 12/2003 | Ivri |
| 6,196,218 B1 | 3/2001 | Voges | | 2004/0000598 A1 | 1/2004 | Ivri |
| 6,196,219 B1 | 3/2001 | Hess et al. | | 2004/0004133 A1 | 1/2004 | Ivri et al. |
| 6,205,999 B1 | 3/2001 | Ivri et al. | | 2004/0011358 A1 | 1/2004 | Smaldone et al. |
| 6,216,916 B1 | 4/2001 | Maddox et al. | | 2004/0035413 A1 | 2/2004 | Smaldone et al. |
| 6,223,746 B1 | 5/2001 | Jewett et al. | | 2004/0035490 A1 | 2/2004 | Power |
| 6,235,177 B1 | 5/2001 | Borland et al. | | 2004/0050947 A1 | 3/2004 | Power et al. |
| 6,254,219 B1 | 7/2001 | Agarwal et al. | | 2004/0139963 A1 | 7/2004 | Ivri et al. |
| 6,269,810 B1 * | 8/2001 | Brooker et al. ........ 128/203.12 | | 2004/0139968 A1 | 7/2004 | Loeffler et al. |
| 6,270,473 B1 | 8/2001 | Schwebel | | 2004/0188534 A1 | 9/2004 | Litherland et al. |
| 6,273,342 B1 | 8/2001 | Terada et al. | | 2004/0194783 A1 | 10/2004 | McAuliffe et al. |
| 6,318,640 B1 | 11/2001 | Coffee | | 2004/0226561 A1 | 11/2004 | Colla et al. |
| 6,328,030 B1 | 12/2001 | Kidwell et al. | | 2004/0226566 A1 | 11/2004 | Gunaratnam et al. |
| 6,328,033 B1 | 12/2001 | Avrahami | | 2004/0256488 A1 | 12/2004 | Loeffler et al. |

| | | | |
|---|---|---|---|
| 2005/0011514 A1 | 1/2005 | Power et al. | |
| 2005/0039746 A1 | 2/2005 | Grychowski et al. | |
| 2005/0139211 A1 | 6/2005 | Alston et al. | |
| 2005/0150496 A1 | 7/2005 | Smaldone | |
| 2005/0211245 A1 | 9/2005 | Smaldone et al. | |
| 2005/0211253 A1 | 9/2005 | Smaldone et al. | |
| 2005/0220763 A1 | 10/2005 | Condos et al. | |
| 2005/0235987 A1 | 10/2005 | Smaldone et al. | |
| 2005/0284469 A1 | 12/2005 | Tobia et al. | |

FOREIGN PATENT DOCUMENTS

| | | | |
|---|---|---|---|
| CH | 555 681 | | 11/1974 |
| DE | 11 03 522 | | 3/1961 |
| DE | 3513628 C1 | * | 10/1986 |
| EP | 0 049 636 A1 | | 4/1982 |
| EP | 0 103 161 A2 | | 3/1984 |
| EP | 0 134 847 A1 | | 3/1985 |
| EP | 0 178 925 A2 | | 4/1986 |
| EP | 0 387 222 A1 | | 9/1990 |
| EP | 0 432 992 A1 | | 6/1991 |
| EP | 0 476 991 B1 | | 3/1992 |
| EP | 0 480 615 A1 | | 4/1992 |
| EP | 0 510 648 A2 | | 10/1992 |
| EP | 0 516 565 A1 | | 12/1992 |
| EP | 0 542 723 A2 | | 5/1993 |
| EP | 0 933 138 A2 | | 4/1999 |
| EP | 0 923 957 A1 | | 6/1999 |
| EP | 1 142 600 A1 | | 10/2001 |
| GB | 973 458 | | 10/1964 |
| GB | 1 454 597 | | 11/1976 |
| GB | 2 073 616 A | | 10/1981 |
| GB | 2 101 500 | | 1/1983 |
| GB | 2 177 623 A | | 1/1987 |
| GB | 2 240 494 A | | 7/1991 |
| GB | 2 272 389 A | | 5/1994 |
| JP | 57-023852 | | 2/1982 |
| JP | 57-105608 | | 7/1982 |
| JP | 58-061857 | | 4/1983 |
| JP | 58-139757 | | 8/1983 |
| JP | 59-142163 A | | 8/1984 |
| JP | 60-004714 | | 1/1985 |
| JP | 61-008357 A | | 1/1986 |
| JP | 61-215059 A | | 9/1986 |
| JP | 02-135169 | | 5/1990 |
| JP | 02-189161 | | 7/1990 |
| JP | 60-07721 A | | 1/1994 |
| WO | WO 92/07600 A1 | | 5/1992 |
| WO | WO 92/11050 A1 | | 9/1992 |
| WO | WO 92/17231 A1 | | 10/1992 |
| WO | WO 93/01404 A1 | | 1/1993 |
| WO | WO 93/10910 A1 | | 6/1993 |
| WO | WO 94/09912 A1 | | 5/1994 |
| WO | WO 96/09229 | | 3/1996 |
| WO | WO 99/17888 | | 4/1999 |
| WO | WO 00/37132 | | 6/2000 |

OTHER PUBLICATIONS

Duarte, Alexander G. et al. "Inhalation Therapy During Mechanical Ventilation" Respiratory Care Clinics of North America, Aerosol Therapy, Jun. 2001, pp. 233-259, vol. 7, No. 2.

Fink, James B. et al. "Aerosol Therapy in Mechanically Ventilated Patients: Recent Advances and New Techniques" Seminars in Respiratory and Critical Care Medicine, 2000, pp. 183-201, vol. 21, No. 3.

Fink, James B. et al. Diagram from and abstract of article entitled "Optimizing efficiency of nebulizers during mechanical ventilation: The effect of placement and type of ventilator circuit" Chest, Oct. 1999, 116:312S.

Jorch, G. Letter to the Editor, "Surfactant Aerosol Treatment of Respiratory Distress Syndrome in Spontaneously Breathing Premature Infants", Pediatric Pulmonology 24: 222-224, 1997, Wiley-Liss, Inc.

Smaldone, G. C. "Aerosolized Antibiotics: Current and Future", Respiratory Care, vol. 45, No. 6, p. 667-675.

Smedsaas-Löfvenbert, A. "Nebulization of Drugs in a Nasal CPAP System", Scandinavian University Press, 1999, Acta Paediatr 88: 89-92, Sweden.

Abys, J.A. et al., "Annealing Behavior of Palladium—Nickel Alloy Electrodeposits," Plating and Surface Finishing, Aug. 1996, pp. 1-7.

Allen, T. *Particle Size Measurement*, Third Edition, Chapman and Hall pp. 167-169 (1981).

Ashgriz, N. et al. "Development of a Controlled Spray Generator" Rev. Sci. Instrum., 1987, pp. 1291-1296, vol. 58, No. 7.

Berglund, R.N., et al. "Generation of Monodisperse Aerosol Standards" Environ. Sci. Technology, Feb. 1973, pp. 147-153, vol. 7, No. 2.

Cipolla, D.C. et al., "Assessment of Aerosol Delivery Systems for Recombinant Human Deoxyribonuclease," S.T.P. Pharma Sciences 4 (1) 50-62, 1994.

Cipolla, D.C. et al., "Characterization of Aerosols of Human Recombinant Deoxyribonuclease I (rhDNase) Generated by Neulizers," Pharmaceutical Research II (4) 491-498, 1994.

Dogan, Aydin PhD, Thesis: "Flexional 'Moonie and Cymbal' Actuators", Penn State University, 1994.

Fink, James B. et al. "Aerosol Drug Therapy," Clinical Practice in Respiratory Care; Chapter 12, pp. 308-342; 1999.

Gaiser Tool Company catalog, pp. 26, 29-30 (1990).

Gonda, I. "Therapeutic Aerosols," Pharmaceutics, The Science of Dosage Form Design, Editor: M.E. Aulton, 341-358, 1988.

Hancock, B.C. et al., "Molecular Mobility of Amorphous Pharmaceutical Solids Below Their Glass Transition Temperatures," Pharmaceutical Research 12, 799-806 (1995).

Heyder, J. et al., "Deposition of particles in the human respiratory tract in the size range 0.005-15 microns," J Aerosol Sci 17: 811-825, 1986.

Hickey, Anthony J. "Pharmaceutical Inhalation Aerosol Technology," Drugs And The Pharmaceutical Science, 1992, pp. 172-173, vol. 54.

Hikayama, H., et al. "Ultrasonic Atomizer with Pump Function" Tech. Rpt. IEICE Japan US88-74:25 (1988).

Maehara, N. et al. "Atomizing rate control of a multi-pinhole-plate ultrasonic atomizer" J. Acoustical Soc. Japan, 1988, pp. 116-121, 44:2.

Maehara, N. et al. "Influence of the vibrating system of a multipinhole-plate ultrasonic nebulizer on its performance" Review of Scientific Instruments, Nov. 1986, p. 2870-2876, vol. 57, No. 1.

Maehara, N. et al. "Influences of liquid's physical properties on the characteristics of a multi-pinhole-plate ultrasonic atomizer" J. Acoustical Soc. Japan 1988, pp. 425-431, 44:6.

Maehara, N. et al. "Optimum Design Procedure for Multi-Pinhole-Plate Ultrasonic Atomizer" Japanese Journal of Applied Physics, 1987, pp. 215-217, vol. 26, Supplement 26-1.

Nogi, T. et al. "Mixture Formation of Fuel Injection System in Gasoline Engine" Nippon Kikai Gakkai Zenkoku Taikai Koenkai Koen Ronbunshu 69:660-662 (1991).

Palla Tech Pd an Pd Alloy Processes-Procedure for the Analysis of Additive IVS in Palla Tech Plating Solutions by HPLC, Technical Bulletin, Electroplating Chemicals & Services, 029-A, Lucent Technologies,, pp. 1-5, 1996.

Siemens, "Servo Ultra Nebulizer 345 Operating Manual," pp. 1-23.

TSI Incorporated product catalog. Vibrating Orifice Aerosol Generator (1989).

Ueha, S., et al. "Mechanism of Ultrasonic Atomization Using a Multi-Pinhole Plate" J. Acoust. Soc. Jpn., 1985, pp. 21-26, (E)6,1.

Wehl, Wolfgang R. "Ink-Jet Printing: The Present State of the Art" for Siemens AG, 1989.

* cited by examiner

AEROSOL DELIVERY APPARATUS AND METHOD FOR PRESSURE-ASSISTED BREATHING SYSTEMS

CROSS REFERENCE TO RELATED APPLICATION

This application is a continuation-in-part of U.S. application Ser. No. 10/828,765, filed Apr. 20, 2004, which is incorporated by reference herein in its entirety.

BACKGROUND OF THE INVENTION

This invention relates to apparatus and methods for delivering aerosol particles, e.g. an aerosolized medicament, to the respiratory system of a subject through an invasive or noninvasive pressure-assisted breathing system. More specifically, one aspect of the invention is directed to apparatus and methods for delivering an aerosolized medicament from a nebulizer to a patient by a pressure-assisted breathing system.

The use of pressure-assisted breathing systems is well-known for the treatment of respiratory disorders and diseases in adults, e.g. infection, obstructive sleep apnea and respiratory insufficiency, and in children, e.g. abnormal breathing resulting from small or collapsible airways, small lung volumes, muscle weakness, respiratory distress syndrome, persistent obstruction following surgery, etc. As used herein, the term “pressure-assisted breathing system” means any artificial ventilation system that applies pressures, usually positive, to gas(es) in or about a patient’s airway during inhalation as a means of augmenting movement of gases into the lungs. The term is intended to include mechanical ventilators and continuous positive airway pressure (“CPAP”) systems, which also includes bi-level positive airway pressure systems. The term is also intended to include both non-invasive and invasive systems. Systems that utilize an endotracheal or tracheostomy tube are examples of invasive pressure-assisted breathing systems. Systems that utilize nasal prongs or a mask are examples of non-invasive pressure-assisted breathing systems.

Pressure-assisted breathing systems utilize positive pressure during inhalation to increase and maintain lung volumes and to decrease the work of breathing by a patient. The positive pressure effectively dilates the airway and prevents its collapse. The delivery of positive airway pressure is accomplished through the use of a positive air flow source, e.g. a mechanical ventilator, that provides oxygen or a gas containing oxygen through a flexible tube connected to a patient interface device. The term “patient interface device” includes nasal prongs (cannula), nasopharyngeal tubes or prongs, an endotracheal tube, tracheostomy tube, mask, etc.

The tubes associated with commercially available pressure-assisted breathing systems create a “circuit” for gas flow by maintaining fluid communication between the elements of the circuit. Tubes can be made of a variety of materials, including but not limited to various plastics, metals and composites and can be rigid or flexible. Tubes can be attached to various elements of the circuit in a detachable mode or a fixed mode using a variety of connectors, adapters, junction devices, etc. These elements are sometimes collectively referred to herein as “junction devices”.

As an example of one such junction device, a mechanical ventilator system may utilize a ventilator circuit comprising an inspiratory tube that conducts a flow of gas from a ventilator and an expiratory tube that conducts a flow of gas back to the ventilator. This circuit (sometimes referred to herein as a “ventilator circuit”) is in fluid communication with a third tube (the “respiratory circuit”) that conducts a flow of gas to the patient interface device through a junction device, usually a tubular member in the shape of a “Y” or “T”. Such a junction device may comprise a first leg attachable to the inspiratory tube of the ventilator circuit, a second leg attachable to the expiratory tube of the ventilator circuit and a third leg attachable to the respiratory circuit. Other junction devices may be used, for example, to connect a nebulizer or a patient interface device to the appropriate circuit of the ventilator system.

Aerosol generators or nebulizers have been used to deliver an aerosol of medication through a ventilator system into the respiratory system of a patient. For example, U.S. Pat. No. 6,615,824, issued Sep. 9, 2003, and in co-pending U.S. patent application Ser. No. 10/465,023, filed Jun. 18, 2003, and Ser. No. 10/284,068, filed Oct. 30, 2002 describe apparatus and methods for connecting a nebulizer to a ventilator circuit to emit a aerosolized medicament directly into the flow of gas being delivered to a patient’s respiratory system. As a result, the gas flows in circuits of ventilator systems are called upon to carry suspended aerosol particles from the aerosol generator to the patient.

It is imperative that a therapeutically effective amount of aerosolized medicament reach the desired sites in the patient’s lungs to achieve a successful treatment, yet it is also desirable that the medicament be delivered in as efficient a manner as possible to minimize losses and waste. Although effective amounts of medicament delivered to a patient’s airways in aerosol form, e.g. by the using a nebulizer connected to a ventilator system, are considerably less than the amounts needed to deliver a therapeutically effective amount of medicament systemically, current systems still exhibit inefficiencies. For example, aerosol particles being carried in the circuits of ventilator systems and other pressure-assisted breathing systems may be trapped on the inner walls of the tubes, deposited at irregular surfaces and obstructions in the tubes or other elements in the circuits, impact the interconnection between tubes of different diameters, or be diverted by sharply angled paths in the circuits. As one specific example, aerosol particles have to “turn corners” when traveling at relatively high flow rates through the sharply angled conduits presented by the “Y”, “T”, and “V”-shaped junction devices currently used in conventional pressure-assisted breathing system circuits. As a result, the aerosol particles may impact the walls of the junction device, and a portion of the particles may be diverted from the primary aerosol flow into various ports or branches in the circuits. As another example, aerosol particles may be deposited at the junction of a patient interface device and the respiratory tube connecting it to the ventilator circuit, or may be diverted or deposited within the patient interface device itself.

Accordingly, it is desirable to find ways to decrease the losses of aerosol particles within pressure-assisted breathing systems. In particular, increasing the efficiency in the delivery of aerosolized medicaments through ventilator systems, and the resulting smaller amounts of medicament required for a treatment, can represent a substantial advantage, particularly when scarce and expensive medicaments are employed.

BRIEF SUMMARY OF THE INVENTION

It has been found in accordance with the present invention that the efficiency of delivery of aerosolized medicaments can be significantly increased by eliminating the sharp angles or corners encountered by the flow of aerosol particles in the circuits of pressure-assisted breathing systems. Specifically, the present invention provides apparatus and methods that increase the efficiency of the delivery of aerosolized medicament to the patient by providing a straight or gently angled path for the flow of aerosol particles from the point at which the aerosol generator introduces aerosol particles into the gas flow to the point at which the aerosol particles enter the patient's respiratory system.

In a preferred embodiment, the present invention provides a pressure-assisted breathing system comprising a flow generator, a circuit connecting the flow generator to a patient's respiratory system and an aerosol generator for emitting aerosol particles of medicament into the circuit, wherein the circuit defines a path for said aerosol particles having a change in angle no greater than 15°, preferably no greater than 12°, and most preferably no change in angle at all.

In one embodiment, the present invention provides a junction device for connecting the various flexible tubes comprising the circuits of a pressure-assisted breathing system. For example, one junction device of the present invention may replace the conventional "Y", "T" or "V"-shaped junction piece that connects the inspiratory tube and expiratory tube of a ventilator circuit to the respiratory circuit. Still another embodiment provides improved nasal prongs (cannula) for delivering aerosolized medicament to a patient.

One preferred embodiment of the present invention provides a junction device comprising (i) a tubular main body member having a straight longitudinal lumen extending its entire length for conducting a first flow of gas carrying aerosol particles; and (ii) a tubular branch member in fluid communication with the longitudinal lumen for conducting a second flow of gas substantially free of said aerosol particles into or out of the longitudinal lumen.

In one embodiment, the junction device further comprises: (iii) a port for attaching an aerosol generator to the main body member so as to introduce the aerosol particles into the first flow of gas. In one preferred embodiment, the aerosol generator is a vibrating aperture-type nebulizer that is preferably positioned in the port so that the vibrating plate of the nebulizer is flush with the internal surface ("wall") of the longitudinal lumen so that the emitted aerosol particles will not drag against the internal surfaces of the lumen.

In one embodiment, the present invention provides a ventilator system comprising a ventilator circuit having an inspiratory tube and an expiratory tube converging at a junction device attached to a respiratory circuit. The junction device comprises (a) a tubular main body member having a straight longitudinal lumen extending from a first end attached to said inspiratory tube to a second end attached to said respiratory circuit, and (b) a tubular branch member having a lumen extending from said longitudinal lumen to a third end attached to said expiratory tube. In another embodiment, the junction device further comprises a port for attaching a nebulizer to the main body member so as to introduce aerosol particles into the longitudinal lumen.

In another embodiment, the present invention provides a ventilator system comprising a ventilator circuit and a patient interface device attached to the ventilator circuit, wherein a nebulizer is positioned between the patient interface device and the ventilator circuit. In still another embodiment, a second nebulizer is positioned in the ventilator circuit on a junction device of the present invention.

In one embodiment, the present invention provides a patient interface device comprising a tubular inlet section having a longitudinal lumen, a pair of nasal cannula, and a tubular forked section connecting the inlet section to the nasal cannula. The longitudinal lumen in the inlet section is in fluid communication with lumens in each prong of the forked section so as to define two substantially parallel paths for the aerosol particles, each path having a change angle from the path defined by the longitudinal lumen no greater than 15°, more preferably no greater than 12°

In one embodiment, the present invention provides a method of delivering aerosolized medicament to a subject's respiratory system comprising the steps of attaching the subject to pressure-assisted breathing system comprising a gas flow generator, a circuit connecting the gas flow generator to the subject's respiratory system and an aerosol generator for emitting aerosol particles of medicament into the circuit, the circuit defining a path for said aerosol particles having a change angle no greater than 15°; preferably no greater than 12°, and most preferably no change in angle at all, and then administering the aerosol particles of medicament to the subject via the pressure-assisted breathing system.

DETAILED DESCRIPTION OF THE INVENTION

Most of the following detailed description is directed to a ventilator embodiment of the invention for illustrative purposes only, it being understood that the invention is not limited to such embodiment and can be applied to other pressure-assisted breathing systems.

Figure 1:
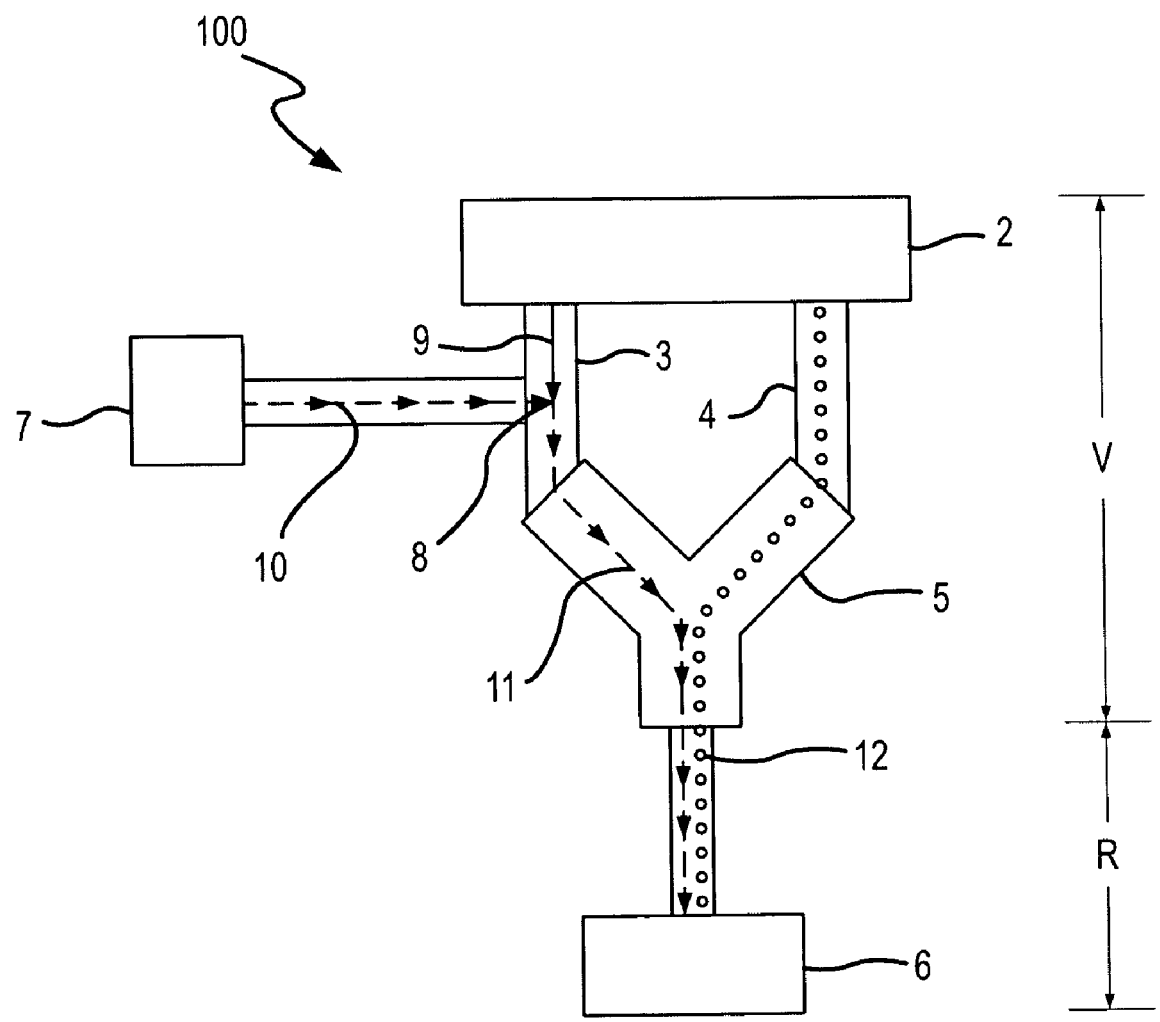
FIG. 1 is a schematic illustration of a pressure-assisted breathing system with a "Y"-shaped junction device.

FIG. 1 of the drawings is a schematic illustration of a ventilator system employing a nebulizer. The ventilator system 100 includes a ventilator circuit V in fluid communication with a respiratory circuit R. One element is in "fluid communication" with another element when it is attached through a channel, port, tube or other conduit that permits the passage of gas, vapor and the like.

Circuit V includes a ventilator 2 in fluid communication with inspiratory tube 3 and expiratory tube 4 converging at "Y"-shaped junction device 5. Respiratory circuit R includes a patient interface device 6 in fluid communication with circuit V at junction device 5. Nebulizer 7 is in fluid communication with circuit V at intersection 8 upstream to junction device 5. In operation, a pressurized flow of gas 9 is introduced into inspiratory tube 3 from ventilator 2 and passes to and through intersection 8. Nebulizer 7 emits an aerosolized medicament 10 into gas flow 9 at intersection 8 to produce combined gas flow 11 containing aerosolized medicament 10. Gas flow 11 is transported through junction device 5 to patient interface device 6 and ultimately to the respiratory system of the patient upon inspiratory effort by the patient through patient interface device 6. Expiratory effort by the patient through patient interface device 6 produces expiratory flow 12 which flows from patient interface device 6 through junction device 5 to expiratory tube 4 and back to ventilator 2.

Figure 2:
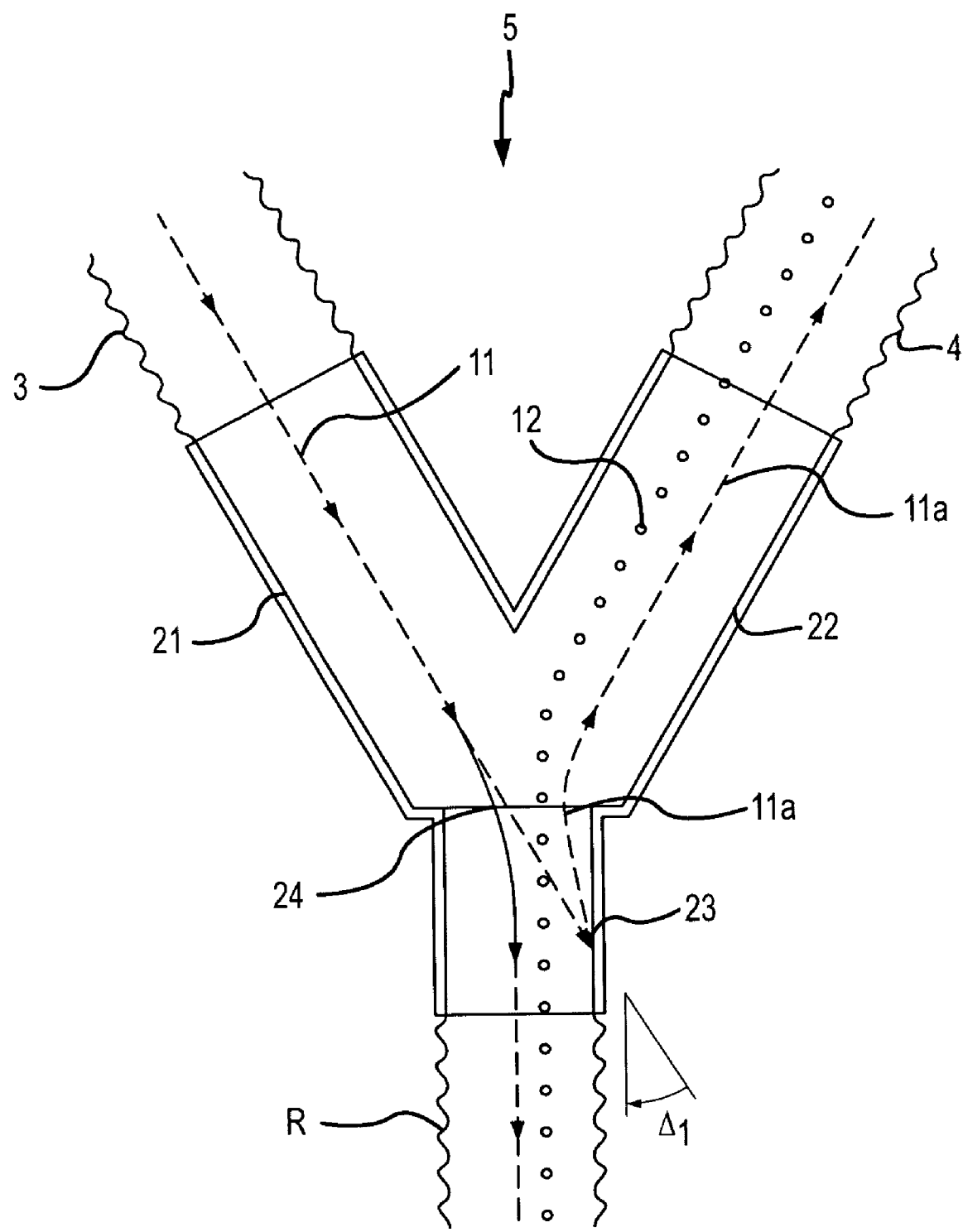
FIG. 2 is a cross-sectional view of the "Y"-shaped junction device of FIG. 1.

Elements in FIG. 2 and subsequent drawings that are similar to those in prior drawings are sometimes assigned the same reference numerals as used in the prior drawings for ease of reference.

Referring now to FIG. 2, junction device 5 comprises inspiratory leg 21 attachable to inspiratory tube 3, expiratory leg 22 attachable to expiratory tube 4 and respiratory leg 23 attachable to respiratory circuit R. Gas flow 11 (containing aerosol particles of medicament 10) passes from inspiratory tube 3 into inspiratory leg 21 and encounters a sharp change in the angle of its path (represented by $\Delta_1$) at intersection 24. As gas flow 11 attempts to turn the sharp corner at intersection 24, a portion of gas flow 11 impacts the wall and ridges encountered at intersection 24. As a result, a portion 11a of gas flow 11 (and the aerosol particles of medicament 10 entrained therein) is diverted to expiratory leg 22 and is lost through expiratory tube 4. The remainder of gas flow 11 continues through respiratory leg 23 to respiratory circuit R. Upon expiratory effort by the patient, expiratory gas flow 12 follows a path from respiratory circuit R through respiratory leg 23, expiratory leg 22 and expiratory tube 4 back to ventilator 2 (not shown).

Figure 3:
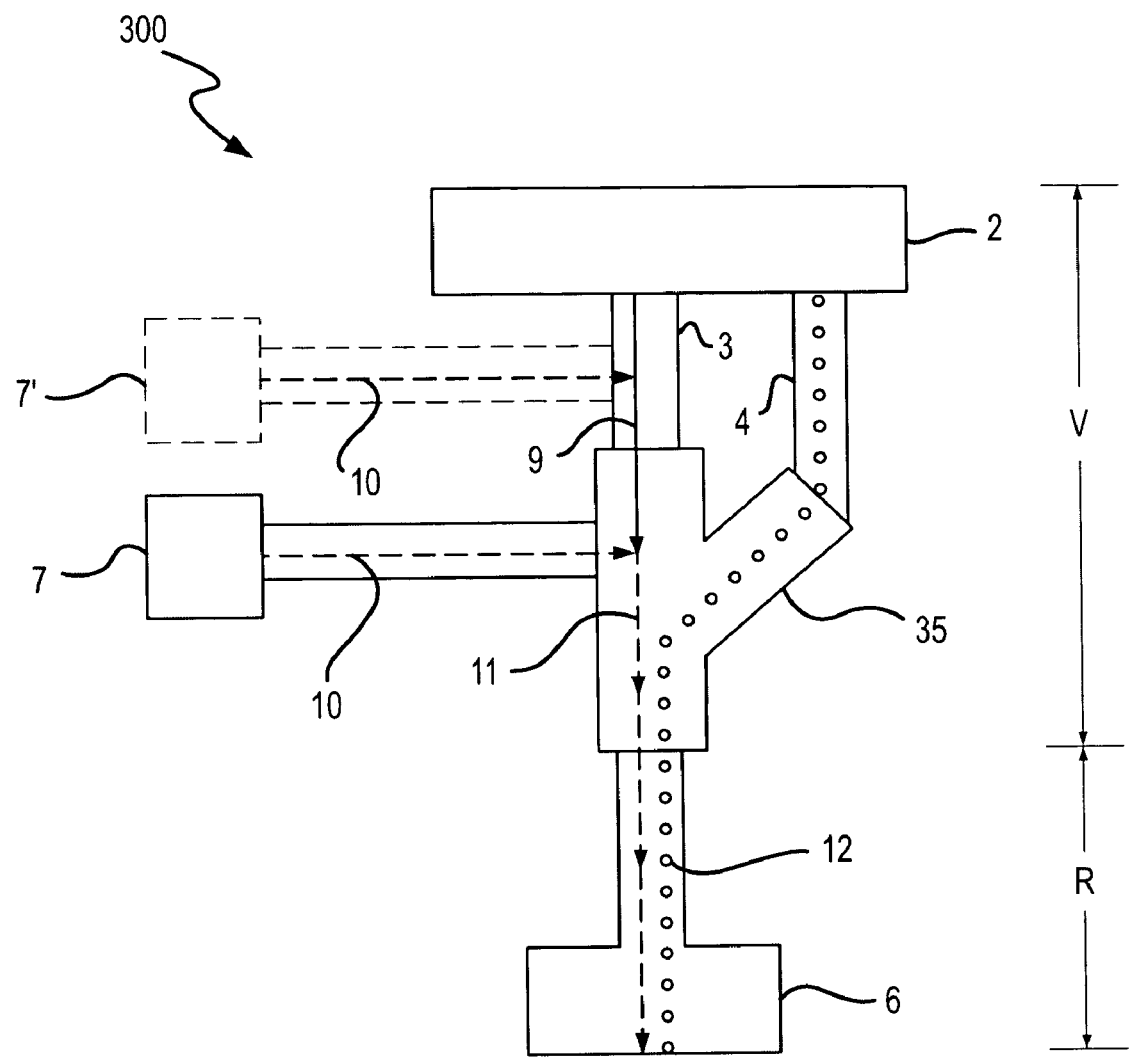
FIG. 3 is a schematic illustration of a pressure-assisted breathing system with a junction device of the present invention.

Referring now to FIG. 3, one embodiment of a mechanical ventilator system in accordance with the present invention will be described. Ventilator system 300 includes a ventilator circuit V and a respiratory circuit R. Ventilator circuit V includes a ventilator 2 in fluid communication with inspiratory tube 3 and expiratory tube 4, which converge at junction device 35 of the present invention. Respiratory circuit R includes a patient interface device 6 in fluid communication with circuit V at junction device 35. Nebulizer 7 may be attached to and in fluid communication with junction device 35. Alternatively, nebulizer 7' may be attached to and in fluid communication with inspiratory tube 3. During operation of ventilator system 300, a pressurized flow of gas 9 is introduced into inspiratory tube 3 from ventilator 2 and passes to and through junction device 35. Nebulizer 7 (or 7') emits an aerosolized medicament 10 into gas flow 9 to produce combined gas flow 11 containing aerosol particles of medicament 10. Gas flow 11 is transported through junction device 35 to patient interface device 6 and ultimately to the respiratory system of the patient. Expiratory effort by the patient through patient interface 6 produces expiratory gas flow 12 which flows from the patient interface device through junction device 35 to expiratory tube 4 back to ventilator 2.

Figure 4:
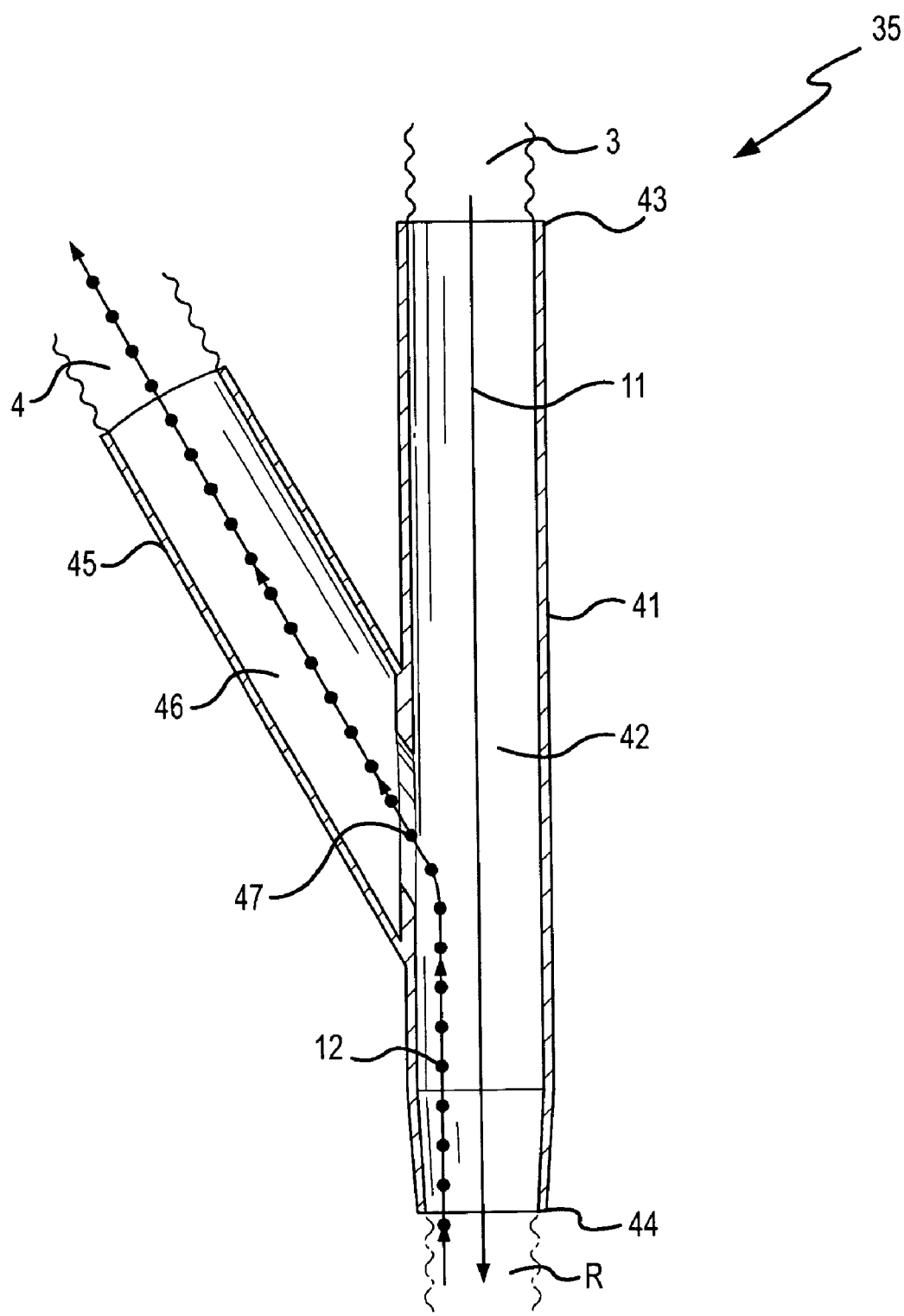
FIG. 4 is a cross-sectional view of a junction device of the present invention.

As illustrated in FIG. 4, one embodiment of junction device 35 may comprise a tubular main body member 41 having a straight longitudinal lumen 42 connecting an opening in a first end 43 attachable to inspiratory tube 3 and an opening in a second end 44 attachable to respiratory circuit R. Junction device 35 may further comprise a tubular branch member 45 having a lumen 46 that communicates with lumen 42 at intermediate opening 47. Gas flow 11, which contains aerosol particles of medicament 10 emitted by nebulizer 7' into gas flow 9 in inspiratory tube 3 (see FIG. 3), passes from inspiratory tube 3 into lumen 42 through the opening in first end 43. In contrast to the "Y"-shaped junction device 5 shown in FIG. 2, junction device 35 provides for gas flow 11 (containing aerosolized medicament 10) to follow a straight unobstructed path to respiratory circuit R without any portion being diverted into branch member 45. In other words, there is virtually no change in the angle of the path of gas flow 11. As a result, the full amount of aerosol particles of medicament contained in gas flow 11 is efficiently delivered through respiratory circuit R to the patient. Upon expiratory effort by the patient, expiratory gas flow 12 follows a path from respiratory circuit R through lumen 42 to lumen 46 of branch member 45 and through expiratory tube 4 back to ventilator 2 (not shown).

Figure 5:
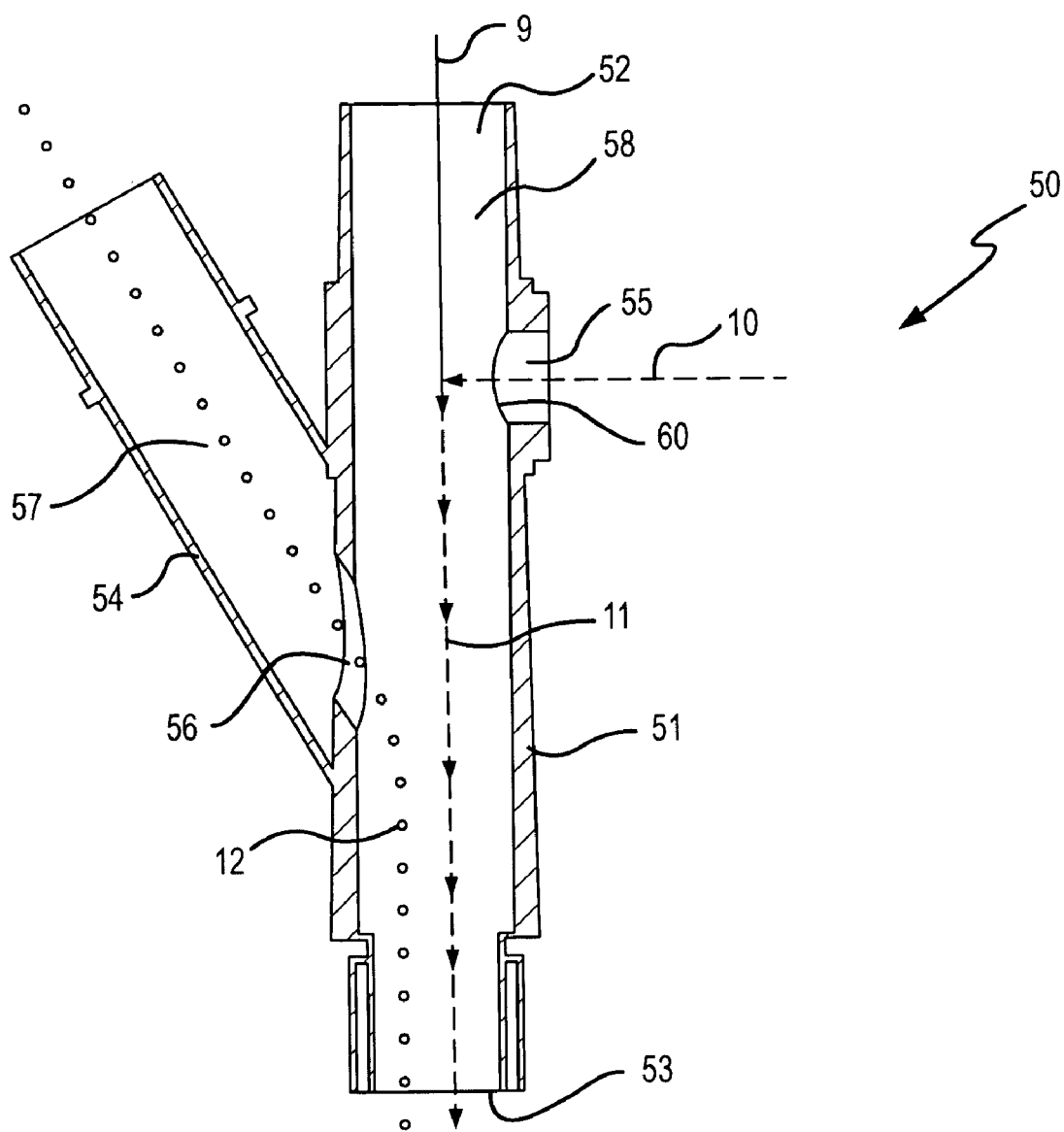
FIG. 5 is a cross-sectional view of another junction device of the present invention.

Another embodiment of the present invention is shown in FIG. 5, wherein junction device 50 comprises tubular main body member 51 having a first end 52 attachable to an inspiratory tube 3 (FIG. 4) and a second end 53 attachable to respiratory circuit R (FIG. 4), a tubular branch member 54 attachable to the expiratory tube 4 (FIG. 4), and a port 55 attachable to a nebulizer (not shown). Gas flow 9 from ventilator 2 (FIG. 3) passes into lumen 58 through the opening in first end 52 of main body 51. Nebulizer 7 (FIG. 3) introduces aerosolized medicament 10 into gas flow 9 in lumen 58 through port 55 located in close proximity to first end 52 of lumen 58. It has been found that any protrusion into lumen 58 causes turbulence in gas flow 9, which may result in the deposition of aerosol particles on the walls of lumen 58. Therefore, if a vibrating aperture-type nebulizer is used, the vibrating plate of the nebulizer is preferably positioned completely within nebulizer port 55, and most preferably flush with the internal surface (wall) of lumen 58. Aerosolized medicament 10 is entrained in gas flow 9 to produce gas flow 11 containing aerosolized medicament 10. Gas flow 11 travels an unobstructed straight path through lumen 58 out the opening in second end 53 to respiratory circuit R. Upon expiratory effort by the patient, expiratory gas flow 12 follows a path from respiratory circuit R through lumen 58 and intermediate opening 56 to lumen 57 of branch member 54 and through expiratory tube 4 back to ventilator 2.

The gas flow generator employed in the present invention may conveniently comprise any of the known sources of pressurized gas suitable for use in a pressure-assisted breathing system. Typically, the gas flow generator is capable of supplying a flow of gas, which includes at least some portion of oxygen, at slightly greater than atmospheric pressure. For example, the source of pressurized gas may be an air blower or a ventilator, or the pressurized gas may originate from a wall supply of air and/or oxygen, such as that found within hospitals and medical facilities, or may originate from a pressurized cylinder of cylinders. The pressurized gas may comprise various known mixtures of oxygen with air, nitrogen, or other gases and may be provided in a single stream or flow.

The respiratory circuit of the present invention may comprise a patient interface and optionally, such customary tubes and connectors as are required to provide fluid communication between the ventilator circuit and the patient interface device. The patient interface device may include any of the known devices for providing gas communication to the patient's respiratory system. By way of example, the patient interface device may include nasal prongs, an oral/ nasal mask, a nasal mask, nasopharyngeal prongs, an endotracheal tube, a tracheostomy tube, a nasopharyngeal tube, and the like.

The nebulizer used in the present invention may be any of the aerosol generators suitable for creating aerosols as liquid droplets or dry particles (referred to herein as "aerosol particles"), for example, atomizers, atomizing catheters, vibrating aperture-type nebulizers, ultrasonic nebulizers, jet nebulizers, etc. Preferred nebulizers may comprise a reservoir for holding a liquid medicament to be delivered to a patient's respiratory system and an aerosol generator for aerosolizing the liquid medicament. The nebulizer is positioned so as to direct aerosol particles into a circuit of the pressure-assisted breathing system. For example, the nebulizer may be connected to a circuit of a ventilator system through a separate connector, a connector integrated with the nebulizer body or a connector integrated with a junction device. Particularly preferred "vibrating aperture-type" nebulizers comprise a vibrational element and dome-shaped aperture plate with tapered holes. When the plate vibrates at a rate of about 100 thousand times per second, a micropumping action causes liquid to be drawn through the tapered holes, creating a low-velocity aerosol with a precisely defined range of droplet sizes. Such nebulizers are commercially available from Aerogen Inc., Mountain View, Calif., and are described in detail in the art, for example, in U.S. Pat. No. 6,615,824, issued Sep. 9, 2003, and in copending U.S. patent application Ser. No. 10/465,023, filed Jun. 18, 2003, and Ser. No. 10/284,068, filed Oct. 30, 2002. The entire disclosures of said patent and applications are incorporated by reference herein.

Due to the increased efficiency of the present invention, the reservoir of the nebulizer may be sized to accommodate a smaller amount of medicament. For example, the reservoir of the nebulizer may have a capacity equal to a single unit dose of medicament, i.e. an amount sufficient for one treatment, and substantially all of the medicament may be delivered to the patient without the need to replenish the reservoir. This is particularly beneficial in respiratory therapies that utilize phospholipid surfactants since these medicaments are scarce, expensive and, because of their high viscosity, are difficult to deliver. The present invention may also eliminate the need to pump medicament from an outside container to the nebulizer, although in some applications of the invention this may be desirable.

The nebulizer may be connected to a controller for controlling operation of, and to supply power to, the aerosol generator. Preferably, the controller and other electronic components are connected with wires, cables and connectors that are small and flexible. In one embodiment, the controller may be integrated in the same enclosure with a CPAP system controller. In this case, the two systems may use the same power supply and communicate electronically. Examples of other components that may also be associated with nebulizers are a timer, status indication means, liquid medicament supply nebule or syringe, etc., all as know by those skilled in the art and described in detail in the aforementioned patent and patent applications.

When used in a ventilator system, the nebulizer may be conveniently positioned in the ventilator circuit or in the respiratory circuit. As one example, the nebulizer may be attached to the inspiratory tube of the ventilator circuit using a separate connector or using a connector integrated with the body of the nebulizer. Such connectors are adapted to provide a conduit for aerosol particles to travel from the aerosol generator of the nebulizer to the gas flow in the ventilator circuit so that the aerosol particles are entrained in the gas flow. As another example, the nebulizer may be attached to a port in a junction device of the present invention, as previously described above in connection with FIG. 5.

Figure 6:
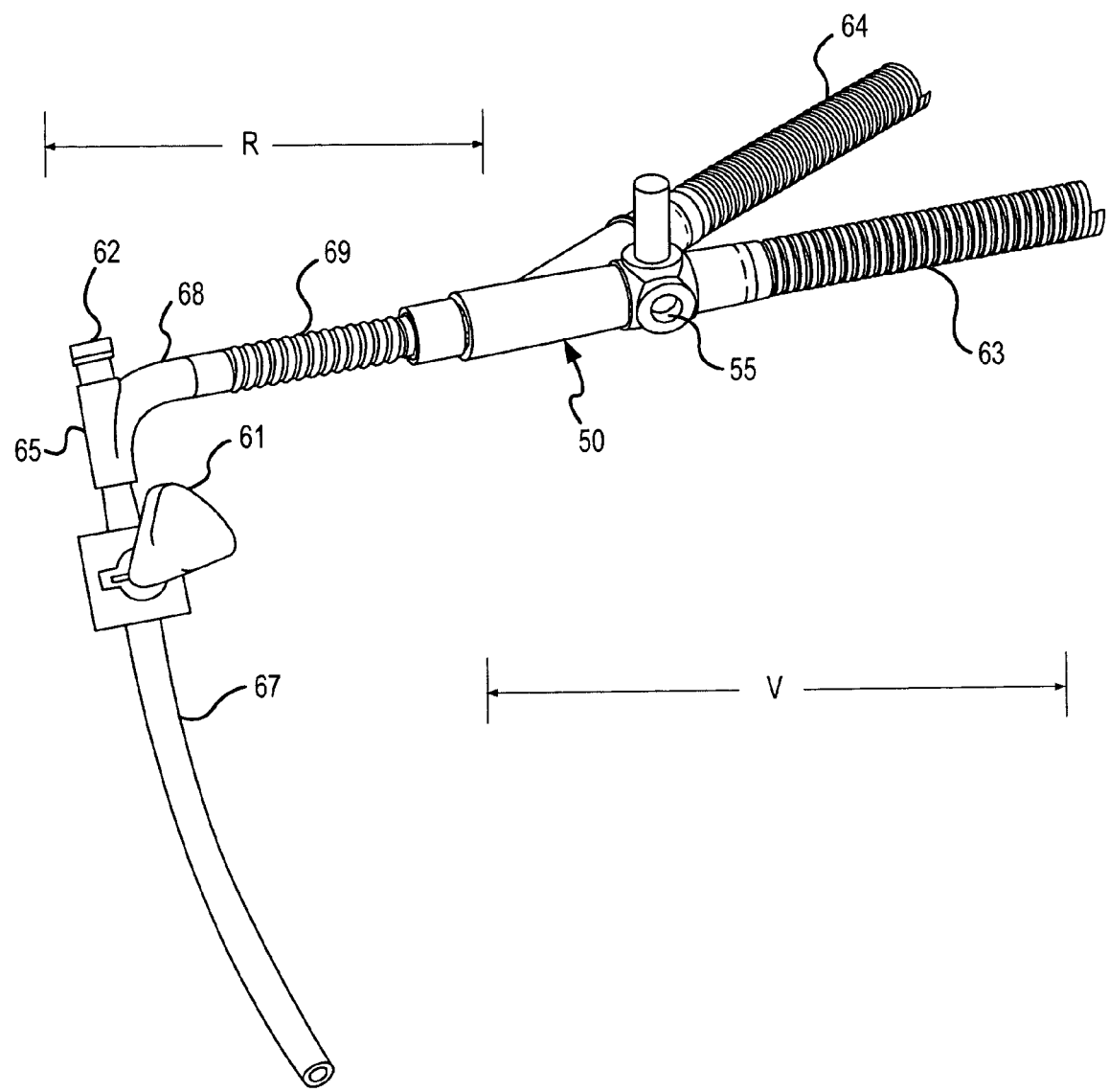
FIG. 6 is a perspective view of the ventilator and respiratory circuits of a pressure-assisted breathing system of the present invention.

For example, FIG. 6 illustrates junction device 50 of FIG. 5 connecting inspiratory tube 63 and an expiratory tube 64 of ventilator circuit V with respiratory tube 69 of respiratory circuit R. When a nebulizer in the ventilator circuit is desired, it may be attached to port 55 of junction device 50, as described in connection with FIG. 5. Alternatively, the nebulizer may be attached to inspiratory tube 63 using one of the previously described connectors.

In other embodiments, it may be advantageous to have a nebulizer positioned in the respiratory circuit. For example, placement of the nebulizer in close proximity to the patient's nose, mouth or artificial airway, e.g. directly adjacent to the point of intake of an endotracheal (ETT) tube or in close proximity to a nasal cannula or mask, may further improve the efficiency and control of the delivery of the aerosolized medicament to the patient. Since significant deposition of aerosol particles may occur at the connection of patient interface device when the aerosol particles impact the edges of the connector as they try to enter the device, placing the nebulizer as close as possible to the patient interface device makes the "dead space" between the aerosol generator and the patient interface device as small as possible. This reduction or elimination of dead space may significantly reduce the loss of aerosol particles entering the patient interface device.

FIG. 6 shows one example of how a nebulizer may be positioned in the respiratory circuit R of a ventilator system. Nebulizer 61 is located between ETT tube 67 and ventilator circuit V, which are connected to each other through connector 65, respiratory tube 69 and junction device 50. In those embodiments wherein a first nebulizer is desired in the respiratory circuit R and a second nebulizer is desired in the ventilator circuit V, the second nebulizer may be optionally attached to junction device 50 using port 55 in the manner described above. Connector 65 is particularly suited for this application because branch member 68 of connector 65 defines an arcuate path for aerosol particles coming through respiratory tube 69 from the second nebulizer attached to junction device 50. This arcuate path minimizes the impact of aerosol particles on the walls of branch member 68 as they travel to ETT tube 67 and, as a result, the loss of aerosol particles at this point is minimized. Connector 65 may also have a port 62 for administering liquids to the patient when such administration is needed.

Figure 7:
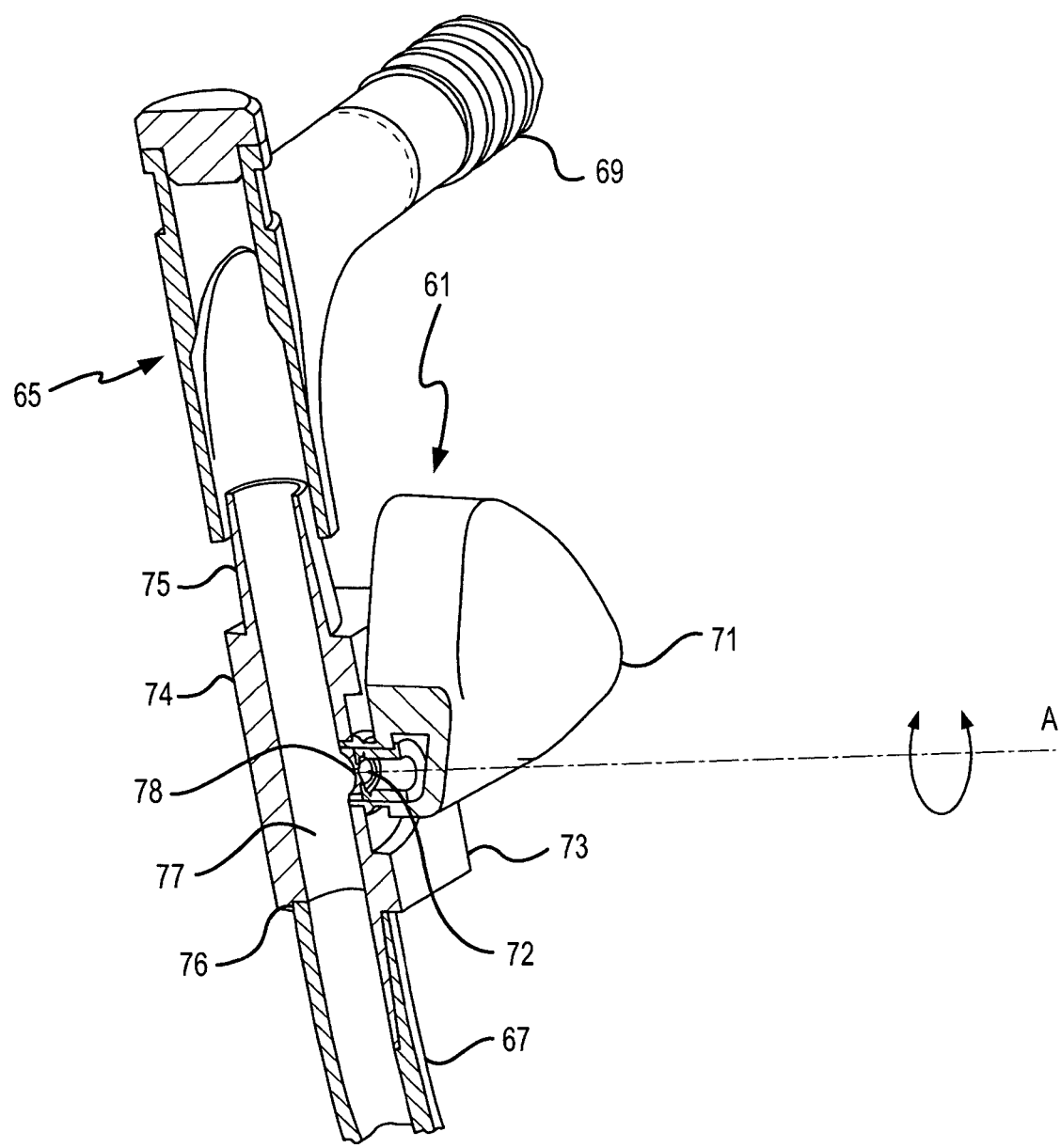
FIG. 7 is a cross-sectional view of the respiratory circuit shown in FIG. 6.

Referring now to FIG. 7, which illustrates an enlarged cross-section of respiratory circuit R in FIG. 6, nebulizer 61 may comprise a reservoir 71 in the shape of a rectangle with rounded corners and connector base 73. Reservoir 71 is adapted to hold liquid medicament for delivery to a patient's respiratory system. Vibrating aperture-type aerosol generator 72 is in fluid communication with reservoir 71 and is adapted to aerosolize liquid medicament that is gravity-fed from reservoir 71. Reservoir 71 is preferably rotatably mounted on connector base 73 so that reservoir 71 can be moved, for example, around an axis represented by A. In this way, reservoir 71 can be readily positioned for optimum gravity feeding of liquid medicament to aerosol generator 72 regardless of varied positions of the patient and/or the other components of the respiratory circuit. For example, when the patient is laying down and ETT tube 67 is in a substantially vertical position, reservoir 71 may be positioned above aerosol generator 72 so that liquid medicament is gravity-fed to aerosol generator 72. If the patient then assumes a sitting position and ETT tube 67 is placed in a substantially horizontal position, reservoir 71 may be rotated 90° to maintain its optimum position above aerosol generator 72 so that liquid medicament continues to be gravity-fed to aerosol generator 72.

Connector base 73 may further comprise main body member 74 having inlet 75 adapted to interconnect with connector 65 on one end and outlet 76 adapted to interconnect with endotracheal tube 67 on the opposite end. Longitudinal lumen 77 extends from inlet 75 through main body member 74 to outlet 76 to form a straight path for the flow of gas from connector 65 to endotracheal tube 67. The vibrating plate of aerosol generator 72 is positioned in port 78 of connector base 73, preferably flush with the internal wall of lumen 77, so as to emit aerosol particles of medicament produced by aerosol generator 72 directly into the gas flow within lumen 77 with a minimum amount of turbulence.

Figure 8:
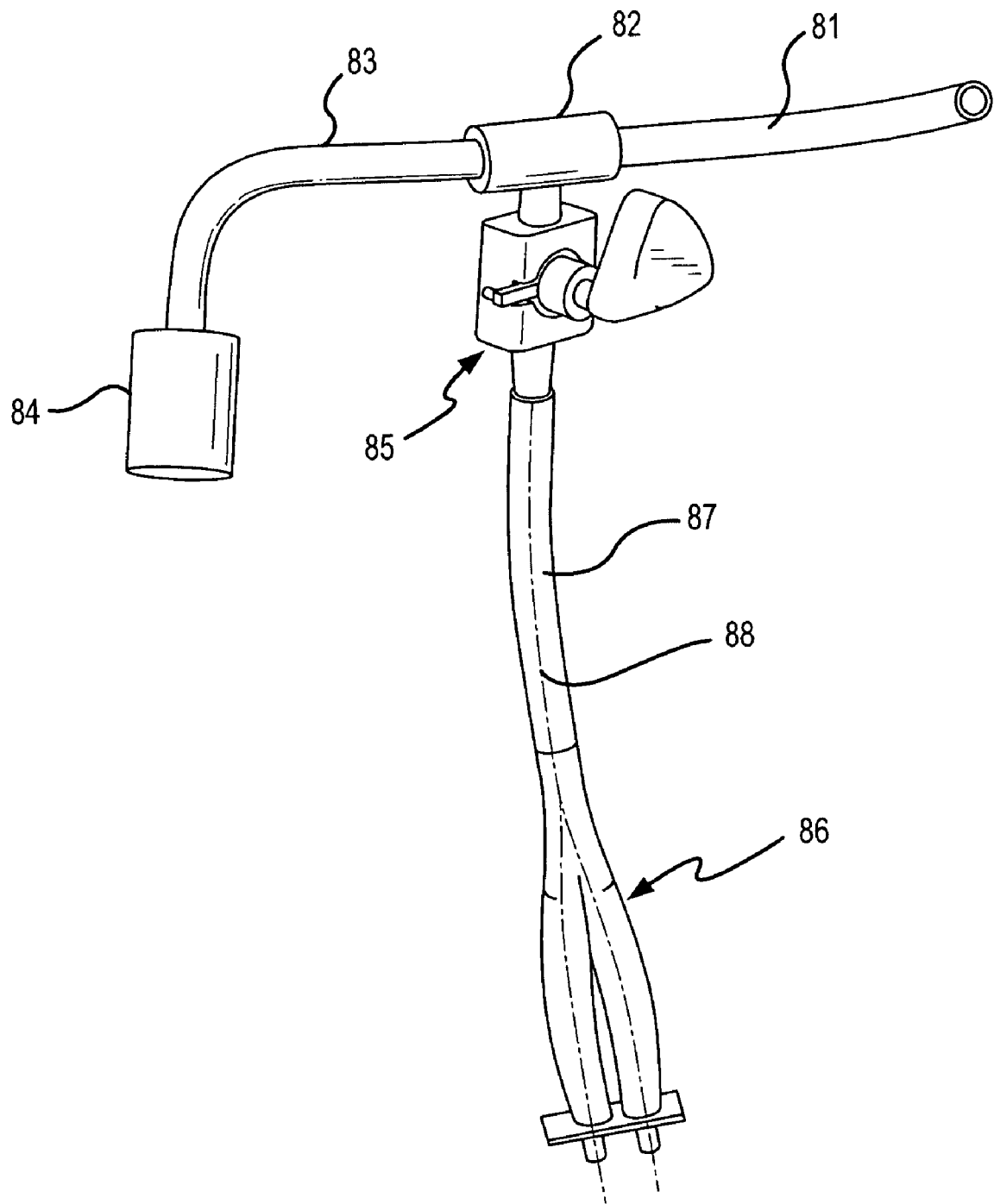
FIG. 8 is a perspective view of a portion of a NCPAP system of the present invention.

FIG. 8 illustrates a neo-natal or infant nasal CPAP ("NC-PAP") system employing nasal cannula according to the present invention. The primary pressure-generating circuit of the CPAP system may comprise flexible tubes 81 and 83 for conducting the high-volume flow of gas generated by a conventional air flow generator (not shown); junction device 82 for connecting tubes 81 and 83 to the respiratory circuit of the CPAP system; and pressure-regulating device 84. Pressure-regulating device 84 may be connected to a controller (not shown) that regulates the level of CPAP in the system. Nebulizer 85 is connected to nasal cannula 86 through respiratory tube 87 and is positioned to emit aerosol particles of medicament into the flow of gas from junction device 82 to nasal cannula 86. Respiratory tube 87 is preferably relatively thin, smaller in diameter and more flexible than flexible tubes 81 and 83. For example, respiratory tube 87 may be commercially available silicone tubing having an outside diameter of about 5 mm. The more flexible nature of respiratory tube 87 allows the patient's head to more freely move about without disconnecting the nasal cannula 86 from the patient. The flow of gas 88 containing aerosol particles is carried through respiratory tube 87 to nasal cannula 86 and ultimately to the patient's nostrils and respiratory system.

Figure 9:
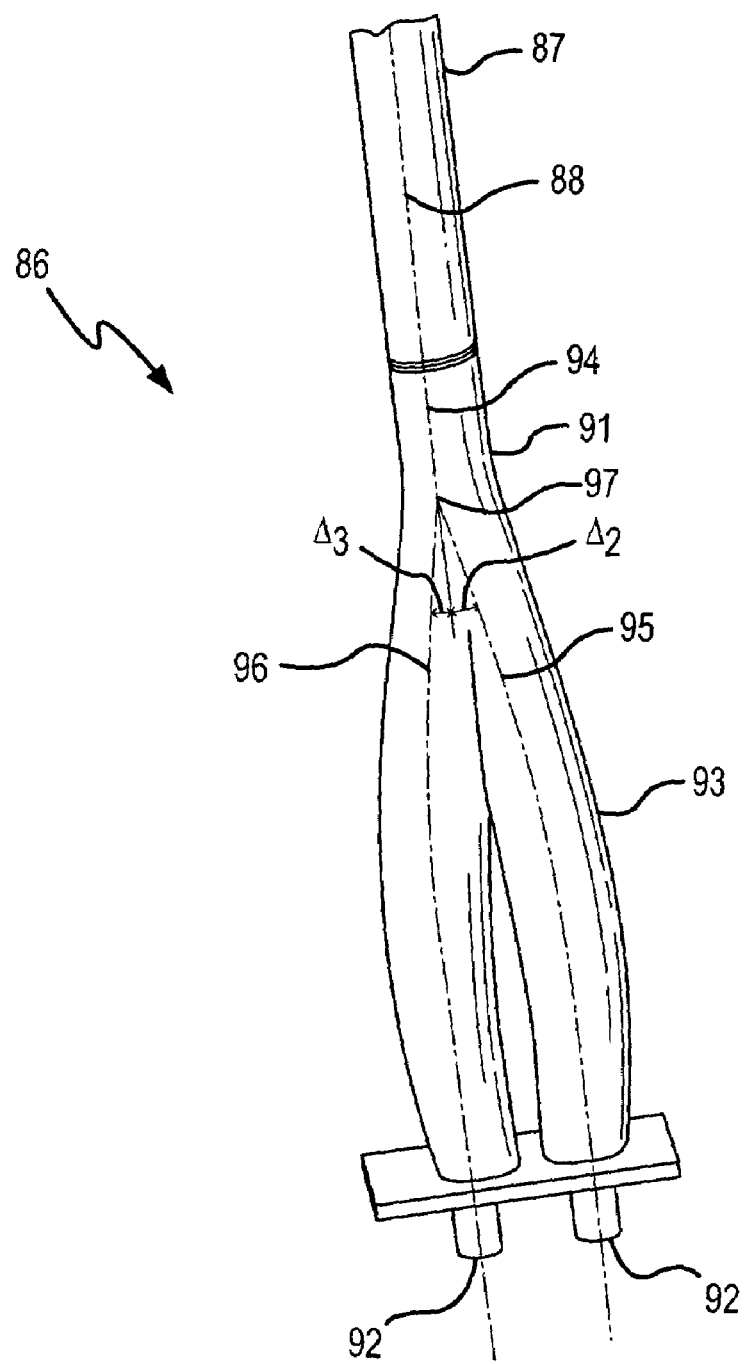
FIG. 9 is a perspective view of the nasal cannula shown in FIG. 8.

Referring now to FIG. 9, nasal cannula 86 of the present invention may comprise a tubular inlet section 91 connected to a pair of nasal cannula 92 by a tubular forked section 93. Lumen 94 in inlet section 91 is in fluid communication with substantially parallel lumens 95 and 96 in each prong of forked section 93 to provide a gently forked conduit extending from inlet section 91 to nasal cannula 92. Air flow 88 containing aerosol particles emitted by nebulizer 85 (FIG. 8) is conducted by respiratory tube 87 through lumen 94 in inlet section 91 to intersection 97, where the path of aerosol particles is split so as to follow lumens 95 and 96 to cannula 92. In accordance with the present invention, the change in angle between the path for aerosol particles defined by lumen 94 and each of the lumens 95 and 96 at intersection 97 is relatively small; i.e. angles $\Delta_2$ and $\Delta_3$ are no greater than about 15°. As a result, substantially all of the aerosol particles of medicament contained in gas flow 88 reach the nasal cannula 92 and ultimately the patient's nostrils. Because there is minimal loss of aerosol particles in the nasal cannula of the present invention, the efficiency of delivery of the aerosolized medicament is significantly enhanced.

The embodiment shown in FIGS. 8 and 9 is particularly useful for treatment of infant respiratory distress syndrome (iRDS). It has been found that early treatment with a surfactant medication by extubation following NCPAP treatment is effective in reducing the mortality and morbidity rates associated with iRDS. Early application of NCPAP and early treatment with surfactant medications are also effective in decreasing the need for mechanical ventilation of infants with iRDS, which may have related adverse effects. For example, see *Pediatrics,* 2004;1 13:e60-563. This embodiment of the present invention provides an efficient way to integrate a vibrating aperture-type aerosol generator with a NCPAP system capable of delivering surfactant medication simultaneously with the CPAP treatment. As a result, the administration of surfactant medication by means of extubation may be eliminated, thereby decreasing the risk of airway damage and secondary infection.

One embodiment of the present invention provides a method of delivering aerosolized medicament to a subject, preferably a human patient that exhibits one or more symptoms of infection or other respiratory disease or disorder. The method generally comprises attaching the subject to a pressure-assisted breathing system comprising a gas flow generator, a circuit connecting the gas flow generator to the subject's respiratory system and an aerosol generator for emitting aerosol particles of medicament into the circuit, wherein the circuit defines a path for the emitted aerosol particles having a change in angle of no greater than 15°. The larger changes of path angle, e.g. about 12°-15°, are most suited to pressure-assisted breathing systems employing nasal cannula, particularly when used with surfactant medications. In other applications, smaller changes of path angle may be preferred, i.e. a change in path angle of no greater than 12° and most preferably no change in path angle (a straight path).

Medicaments useful in the practice of the invention may be any of those commonly used in aerosol form for treating the above-described symptoms, for example, various antibiotics or combinations of antibiotics (preferably used in ventilator systems) and surfactant medicaments (preferably used in CPAP systems). Examples of antibiotics include anti-gram-positive agents such as macrolides, e.g. erythromycin, clarithromycin, azithromycin, and glycopeptides, e.g. vancomycin and teicoplanin, as well as any other anti-gram-positive agent capable of being dissolved or suspended and employed as a suitable aerosol, e.g. oxazoldinone, quinupristin/dalfopristen, etc. Antibiotics useful as anti-gram-negative agents may include aminoglycosides, e.g. gentamicin, tobramycin, amikacin, streptomycin, netilmicin, quinolones, e.g. ciprofloxacin, ofloxacin, levofloxacin, tetracyclines, e.g. oxytetracycline, dioxycycline, minocycline, and cotrimoxazole, as well as any other anti-gram-negative agents capable of being dissolved or suspended and employed as a suitable aerosol.

Surfactant medications (sometimes referred to herein as "surfactants") are protein-lipid compositions, e.g. phospholipids, that are produced naturally in the lungs and are essential to the lungs' ability to absorb oxygen. They facilitate respiration by continually modifying surface tension of the fluid normally present within the air sacs, or alveoli, that tube the inside of the lungs. In the absence of sufficient surfactant, these air sacs tend to collapse, and, as a result, the lungs do not absorb sufficient oxygen. Insufficient surfactant in the lungs results in a variety of respiratory illnesses in both animals and humans. Since most of these surfactant medications are animal-based, the current supply is limited, and although synthetic surfactants are available, their manufacture is both inexact and expensive. In addition, the surfactant medications are typically high in viscosity and are difficult to deliver to the patient's respiratory system. The increased efficiency of the pressure-assisted breathing system of the present invention, and the smaller amount of medicament required for a treatment according to the present invention, can be a substantial advantage when such scarce and expensive medicaments are employed.

In a preferred embodiment, the nebulizer of the present invention has a reservoir capacity equal to a unit dose of medicament. As an example, one dose of a liquid phospholipid surfactant medicament is typically achieved by instilling about 100 mg of the surfactant into an infant's lung. However, the required aerosol dose appears to be considerably less. For example, animal researchers have determined that an inhaled dose of about 4.5 mg/kg of surfactant is sufficient to substantially improve oxygenation in animal models. This suggests that a sufficient unit dose of surfactant to deliver to the lungs of a 1 kg. infant in aerosolized form may be about 5-10 mg. Since liquid surfactant is typically dispensed in a dilute solution having a concentration of 25 mg/ml, about $\frac{2}{5}$ ml ($\frac{10}{25}$ ml) of liquid surfactant may be required to obtain 10 mg of active surfactant. A neonate CPAP system may be designed according the present invention to deliver about 6-18% of the total aerosolized medicament to an infant's lungs with a normal breathing pattern. If, for example, the nebulizer efficiency is 10%, the amount of surfactant solution required in the nebulizer reservoir to deliver a unit dose of aerosolized surfactant would have to be increased by a factor of 10, i.e. 10×$\frac{2}{5}$ ml or 4 ml. Therefore, a nebulizer reservoir having a capacity of 4 ml may be sufficient to provide a unit dose of surfactant to a 1 kg infant in accordance with the present invention without the need to replenish the reservoir.

The unit dose and the corresponding nebulizer reservoir size may vary depending on the efficiency of the nebulizer, the weight of the patient and the amount of surfactant needed. For example, if the infant in the above example weighs 3 kg, a unit dose (and corresponding reservoir size) would be about 12 ml of liquid surfactant (i.e. 3 kg×4 ml/kg). Similarly, if 5 mg of active surfactant is needed in the above example, a unit dose would be about 2 ml of liquid surfactant (i.e. $\frac{5}{25}$ ml×10), and if the efficiency of the nebulizer in the above example is 15%, a unit dose would be about $2\frac{2}{3}$ ml (i.e. $\frac{2}{5}$ ml×$\frac{100}{15}$).

A nebulizer according to the present invention may administer a unit dose by aerosol in less than 20 minutes, and possibly in as little as 5 minutes. Aerosol generation can be continuous or phasic, and can be timed to titrated dose delivery rate over time; for example, a 4 ml maximum dose with nebulization for 1 second out of every 10, 20 or 30 seconds.

The pressure-assisted breathing systems of the present invention may include any of the other elements conventionally found in such systems such as, for example, humidifiers, filters, gauges, traps for sputum and other secretions and controllers that control the breathing cycle, the nebulizer and/or other components. An humidifier in the system is particularly advantageous since control of the humidity may affect the efficiency of aerosol particle delivery. For examples, the aerosol particles should be prevented from undergoing significant hygroscopic enlargement since particles enrobed in water will tend to condense of the walls of system tubes. Breathing cycle controllers may also be particularly useful in the practice of the invention since they may be used to actuate the administration of aerosol only during the inspiration phase of the breathing cycle or when the humidifier is not active, thereby further enhancing the efficiency of the system.

It is understood that while the invention has been described above in connection with preferred specific embodiments, the description and drawings are intended to illustrate and not limit the scope of the invention, which is defined by the appended claims and their equivalents.

What is claimed is:

1. A pressure-assisted breathing system comprising:
an air flow generator;
a circuit connecting the air flow generator to a patient's respiratory system; and
an aerosol generator for emitting aerosol particles into the circuit;
wherein the circuit defines a path from the point at which the aerosol generator emits aerosol particles into the circuit to the point at which the aerosol particles enter the patient's respiratory system, the path having a change in angle of no greater than 15°.

2. A system according to claim 1 wherein the change in path angle is no greater than 12°.

3. A system according to claim 1 wherein the circuit defines a straight path for the emitted aerosol particles.

4. A system according to claim 1 wherein the circuit comprises a ventilator system.

5. A system according to claim 1 wherein the circuit comprises a CPAP system.

6. A system according to claim 1 wherein the aerosol generator comprises a nebulizer.

7. A system according to claim 6 wherein the nebulizer comprises a reservoir for holding a liquid medicament to be delivered to the patient's respiratory system and a vibrating aperture-type aerosol generator for aerosolizing the liquid medicament.

8. A system according to claim 7 wherein the reservoir has a capacity equal to one unit dose of medicament.

9. A system according to claim 7 wherein the reservoir is rotatable to maintain optimum gravity feeding of liquid medicament to the aerosol generator during varied positions of the patient and/or the other components of the circuit.

10. A system according to claim 1 wherein the circuit comprises a ventilator circuit having a inspiratory tube and a expiratory tube converging on a junction device connected to a respiratory circuit, the junction device having: (a) a tubular main body member having a straight longitudinal lumen extending from a first end attached to the inspiratory tube to a second end attached to the respiratory circuit; and (b) a tubular branch member having a lumen extending from the longitudinal lumen to a third end attached to the expiratory tube.

11. A system according to claim 10 wherein the aerosol generator is positioned to emit aerosol particles into the inspiratory tube.

12. A system according to claim 10 wherein the aerosol generator is positioned to emit aerosol particles into the longitudinal lumen of the junction device.

13. A system according to claim 1 wherein said circuit comprises a ventilator circuit and a patient interface device attached to the ventilator circuit.

14. A system according to claim 13 wherein the aerosol generator is a nebulizer positioned to emit aerosol particles into the circuit between the ventilator circuit and the patient interface device.

15. A system according to claim 14 wherein the aerosol generator is located in the direct vicinity of the patient's nose, mouth or artificial airway.

16. A system according to claim 13 wherein the patient interface device comprises a tubular inlet section connected to a pair of nasal cannula by a tubular forked section, wherein a lumen in the inlet section is in fluid communication with lumens in each prong of the forked section so as to provide two substantially parallel paths for aerosol particles passing therethrough, each path having a change of angle no greater than 15°.

17. A patient interface device for the delivery of aerosol particles to a patient comprising:
    a tubular inlet section having a longitudinal lumen;
    a pair of nasal cannula; and
    a tubular forked section connecting the inlet section to the nasal cannula;
    wherein the longitudinal lumen is in fluid communication with lumens in each prong of the forked section so as to conduct the aerosol particles along two paths from the point of entry of the aerosol particles into the patient interface device to the point at which the aerosol particles enter the patient's respiratory system, each path having a change of angle no greater than 15°.

18. An NCPAP system comprising:
    (a) a pressure-generating circuit;
    (b) a patient interface device connected to the pressure-generating circuit for conducting a pressurized flow of gas from the pressure-generating circuit to a patient;
    said patient interface device comprising:
        (i) a tubular inlet section having a longitudinal lumen;
        (ii) a pair of nasal cannula; and
        (iii) a tubular forked section connecting the inlet section to the nasal cannula; and
    (c) a nebulizer positioned between the pressure-generating circuit and the patient interface device so as to emit aerosol particles of medicament into the flow of gas to the patient interface device,
    wherein the longitudinal lumen is in fluid communication with lumens in each prong of the forked section so as to conduct the aerosol particles along two paths from the point of entry of the emitted aerosol particles into the patient interface device to the point at which the aerosol particles enter the patient's respiratory system, each path having a change of angle no greater than 15°.

19. A method of delivering an aerosolized medicament to a subject's respiratory system comprising the steps of:
    attaching the subject to a pressure-assisted breathing system comprising:
    an air flow generator;
    a circuit connecting the air flow generator to the subject's respiratory system; and
    an aerosol generator for emitting aerosol particles of medicament into the circuit;
    wherein the circuit defines a path from the point at which the aerosol generator emits aerosol particles into the circuit to the point at which the aerosol particles enter the subject's respiratory system, said path having a change in angle of no greater than 15°; and
    administering the aerosol particles of medicament to said subject via the pressure-assisted breathing system.

20. A method according to claim 19 wherein the pressure-assisted breathing system is a mechanical ventilator system comprising a ventilator circuit having an inspiratory tube and a expiratory tube converging on a junction device connected to a respiratory circuit comprising a patient interface device; the junction device comprising:
    (a) a tubular main body member having a straight longitudinal lumen extending from a first end attached to the inspiratory tube to a second end attached to the respiratory circuit; and
    (b) a tubular branch member having a lumen extending from the longitudinal lumen to a third end attached to the expiratory tube.

21. A method according to claim 20 wherein the aerosol particles of medicament are introduced into the inspiratory tube of the ventilator circuit or into the longitudinal lumen of the junction device.

22. A method according to claim 20 wherein the aerosol particles of medicament are introduced into the respiratory circuit in direct proximity to the patient's mouth, nose or artificial airway.

23. A method according to claim 20 wherein the subject is a patient exhibiting one or more symptoms of infection and the medicament is an antibiotic.

24. A method according to claim 19 wherein the pressure-assisted breathing system is a NCPAP system comprising:
    (a) a pressure-generating circuit;
    (b) a patient interface device connected to the pressure-generating circuit for conducting a pressurized flow of gas from the pressure-generating circuit to a patient;
    said patient interface device comprising:
        (i) a tubular inlet section having a longitudinal lumen;
        (ii) a pair of nasal cannula; and
        (iii) a tubular forked section connecting the inlet section to the nasal cannula; wherein the longitudinal lumen is in fluid communication with lumens in each prong of the forked section so as to conduct the flow of gas along two substantially parallel paths to the nasal cannula, each path having a change of angle no greater than 15°; and
    (c) a nebulizer positioned between the pressure-generating circuit and the patient interface device so as to emit aerosol particles of medicament into the flow of gas to the patient interface device.

25. A method according to claim 24 wherein the patient is an infant exhibiting one or more symptoms of infant respiratory distress syndrome and the medicament is a surfactant.

26. A method of treating infant respiratory distress syndrome comprising the steps of:
    (a) attaching the infant to a NCPAP system comprising:
        (i) a pressure-generating circuit;
        (ii) a respiratory circuit that conducts a pressurized gas flow from the pressure-generating circuit to a nasal cannula patient interface device, and
        (iii) a vibrating aperture-type nebulizer in fluid communication with the respiratory circuit so as to introduce aerosol particles of surfactant medication into the pressurized gas flow in the respiratory circuit; wherein the nasal cannula interface device defines a path for the aerosol particles from the point of entry of the aerosol particles into the nasal cannula interface device to the point of entry of the aerosol particles into the infant's respiratory system, said path having a changed in angle no greater than 15°; and
    (b) administering the aerosol particles of surfactant medicament to the infant via the nasal cannula interface device.

* * * * *